United States Patent [19]

Burow, Jr.

[11] Patent Number: 4,500,343

[45] Date of Patent: Feb. 19, 1985

[54] OXAZOLYL AND THIAZOLYL AMIDES AS HERBICIDES

[75] Inventor: Kenneth W. Burow, Jr., Indianapolis, Ind.

[73] Assignee: Eli Lilly and Company, Indianapolis, Ind.

[21] Appl. No.: 429,765

[22] Filed: Sep. 30, 1982

[51] Int. Cl.³ .................. A01N 43/74; A01N 43/80; A01N 43/82

[52] U.S. Cl. ........................... 71/76; 71/88; 71/90; 548/245; 548/246; 548/214; 548/233; 548/133; 548/143; 548/195; 548/550; 548/551

[58] Field of Search ............... 548/245, 246, 214

[56] References Cited

U.S. PATENT DOCUMENTS

| | | | |
|---|---|---|---|
| 3,311,614 | 3/1967 | Capps | 260/239.3 |
| 3,981,714 | 9/1976 | Metzger et al. | 71/90 |
| 4,013,675 | 3/1977 | Deli et al. | 260/306.8 A |
| 4,021,224 | 5/1977 | Pallos et al. | 548/245 |
| 4,075,001 | 2/1978 | Gibbon | 71/90 |
| 4,122,183 | 10/1978 | Neville et al. | 424/272 |
| 4,143,047 | 3/1979 | Harrison | 260/307 |
| 4,158,659 | 6/1979 | Ross et al. | 260/307 |
| 4,166,818 | 9/1979 | Ross et al. | 548/128 |
| 4,337,081 | 6/1982 | Gay | 71/90 |

FOREIGN PATENT DOCUMENTS

| | | | |
|---|---|---|---|
| 778198 | 1/1971 | Belgium . | |
| 613501 | 1/1961 | Canada | 71/88 |
| 1954179 | 5/1971 | Fed. Rep. of Germany | 548/214 |
| 2828265 | 6/1978 | Fed. Rep. of Germany . | |
| 5691 | 4/1964 | Japan | 548/242 |
| 1226913 | 6/1969 | United Kingdom | 548/214 |
| 1226913 | 3/1971 | United Kingdom | 548/214 |
| 1275267 | 5/1972 | United Kingdom . | |
| 1590870 | 7/1974 | United Kingdom | 548/245 |
| 1529469 | 10/1978 | United Kingdom . | |
| 1532239 | 11/1978 | United Kingdom . | |
| 1548397 | 7/1979 | United Kingdom | 548/214 |
| 1590870 | 6/1981 | United Kingdom . | |

OTHER PUBLICATIONS

Srivastava et al., "Some derivatives . . . anaesthetic." Eur. J. Med. Chem. 15, No. 3, p. 274, (1980).
Chemical Abstract 96: 122561M.
Paul et al., "Zur Synthese . . . Pyrrolidone-(2)", Arch. Pharm. (Weinhem) 315, pp. 17-22, (1982).
Beattie, et al., "Gastric . . . 4-acylaminothiazoles." Eur. J. Med. Chem. 14, pp. 105-110, (1979).
Derwent Abstract 48610T.
Derwent Abstract 05558C.

*Primary Examiner*—Donald G. Daus
*Assistant Examiner*—G. Hendricks
*Attorney, Agent, or Firm*—Joseph A. Jones; Arthur R. Whale

[57] ABSTRACT

1-Heterocyclic-2-pyrrolidinone analogs, and intermediates thereof, as aquatic and terrestrial herbicides and aquatic algicides. The compounds and intermediates can also be used together with one or more herbicides to provide useful terrestrial herbicidal combinations.

3 Claims, No Drawings

OXAZOLYL AND THIAZOLYL AMIDES AS HERBICIDES

SUMMARY OF THE INVENTION

The present invention relates to a compound of the formula

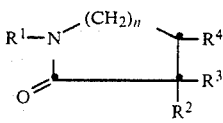

wherein:
$R^1$ is

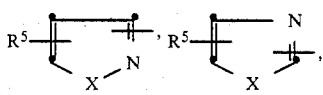

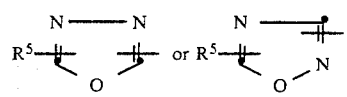

each $R^2$ and $R^3$ independently are hydrogen, halogen or $C_1$–$C_6$ alkyl;
$R^4$ is hydrogen or $C_1$–$C_4$ alkyl;
$R^5$ is $C_3$–$C_{10}$ alkyl, $C_1$–$C_4$ haloalkyl, $C_3$–$C_8$ cycloalkyl or $C_1$–$C_4$ alkyl substituted $C_3$–$C_8$ cycloalkyl;
n is 1, 2 or 3; and
X is O or S.

Compositions containing these compounds are also disclosed, as well as methods for their use.

An additional embodiment of the present invention relates to an intermediate of the formula

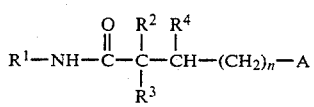

wherein:
$R^1$ is

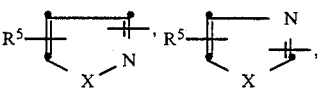

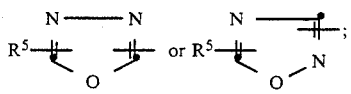

each $R^2$ and $R^3$ independently are hydrogen, halogen or $C_1$–$C_6$ alkyl;
$R^4$ is hydrogen or $C_1$–$C_4$ alkyl;
$R^5$ is $C_3$–$C_{10}$ alkyl, $C_1$–$C_4$ haloalkyl, $C_3$–$C_8$ cycloalkyl or $C_1$–$C_4$ alkyl substituted $C_3$–$C_8$ cycloalkyl;
n is 1, 2 or 3;
X is O or S; and
A is halogen.

These intermediates are useful both as herbicides and intermediates to the above described cyclized derivatives.

In addition to being terrestrial herbicides, the present compounds and intermediates are also aquatic herbicides and algicides.

The present invention also provides herbicidal combinations comprising a present compound or intermediate together with one or more herbicides.

DETAILED DESCRIPTION OF THE INVENTION

In the above formulas, $C_3$–$C_{10}$ alkyl represents a straight or branched alkyl chain having from three to ten carbon atoms. Typical $C_3$–$C_{10}$ alkyl groups include n-propyl, isopropyl, n-butyl, sec.-butyl, isobutyl, t-butyl, n-pentyl, isopentyl, sec.-pentyl, neopentyl, n-hexyl, sec.-hexyl, isohexyl, n-heptyl, isoheptyl, sec.-heptyl, n-octyl, sec.-octyl, isooctyl, n-nonyl, sec.-nonyl, isononyl, n-decyl, sec.-decyl, and the like. $C_4$–$C_7$ Alkyl is preferred.

$C_3$–$C_8$ Cycloalkyl represents saturated monocyclic cycloalkyl groups such as cyclopropyl, cyclobutyl, cyclopentyl, cyclohexyl, cycloheptyl, and cyclooctyl.

The term "halogen", as defined herein, represents fluorine, chlorine, bromine and iodine. Preferred halogen atoms are chlorine and bromine.

The term "$C_1$–$C_4$ alkyl substituted $C_3$–$C_8$ cycloalkyl" includes 2-methylcyclopropyl, 2,3-dimethylcyclopropyl, 2-isopropylcyclopropyl, 2-t-butylcyclopropyl, 2-ethylcyclobutyl, 1,2-dimethyl-3,4-dipropylcyclobutyl, 2-sec.-butylcyclopentyl, 3,3-dimethylcyclopentyl, 2-ethyl-4-butylcyclohexyl, 3-isobutyl-4,4-diethylcyclohexyl, 2,3,4-trimethyl-5-ethylcycloheptyl, 1-propyl-6-ethylcycloheptyl, 4-n-butylcyclooctyl, 5,6-diethylcyclooctyl, and the like.

$C_1$–$C_4$ haloalkyl is a $C_1$–$C_4$ alkyl group bearing one or more halogen substituents. Such haloalkyl groups include trifluoromethyl, 1,1,2,2-tetrafluoroethyl, pentabromoethyl, pentafluoroethyl, 3,3,3-trichloropropyl, 1-iodobutyl and the like.

Preferred compounds and intermediates have the above formulas wherein

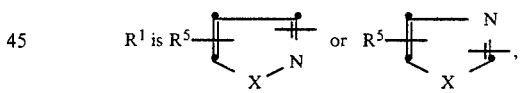

each $R^2$ and $R^3$ independently are hydrogen or methyl and n is one or two. Particularly preferred compounds and intermediates have the above formulas wherein

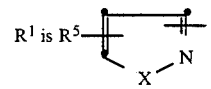

and X is oxygen.

The compounds and intermediates of the present invention are prepared by procedures well known to those skilled in the art. The preferred process involves reacting an appropriate heterocyclic amine with a halogen substituted carboxylic acid derivative to provide the corresponding intermediate halogen substituted-N-heterocyclic carboxylic acid amide, which is finally cyclized in the presence of an acid acceptor to give the appropriate N-heterocyclic pyrrolidinone analog. The reaction scheme for this process is as follows.

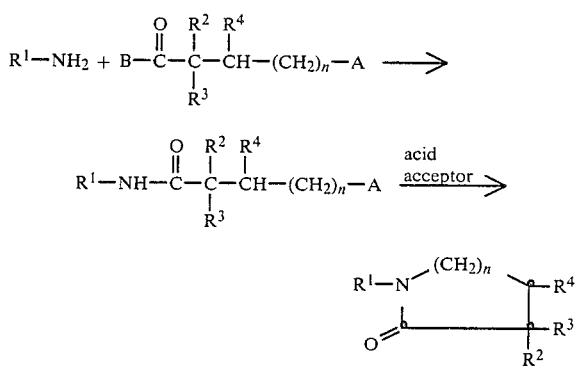

wherein $R^1$, $R^2$, $R^3$, $R^4$, A and n are as defined above and B is halogen, hydroxy, $C_1$-$C_6$ alkoxy,

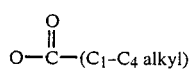

and the like.

The condensation of the heterocyclic amine with a halogen substituted carboxylic acid derivative is carried out by combining approximately equimolar quantities of the two starting materials in a suitable solvent. Suitable solvents include the aprotic solvents, preferably ethyl acetate, toluene and benzene. When the by-product of this reaction is an acid, it is necessary to add an acid acceptor to the reaction mixture, for example when B in the above formula is halogen. The reaction may also be carried out in an inert atmosphere such as nitrogen or argon. Exemplary acid binding agents include most organic bases. The preferred base is triethylamine. When B in the above formula is hydroxy, an activating reagent must be used. Suitable activating reagents include CDI (carbonyldiimidazole), DCC (N,N'-dicyclocarbodiimide) and the like. The reaction is performed at temperatures between 0° C. and 150° C., more preferably between 15° C. and the reflux temperature of the reaction mixture. The product is isolated by typically filtering off the salts produced in the reaction and removing the volatiles by evaporation under reduced pressure. The compound thus isolated may be further purified if desired by procedures well known in the art such as crystallization from common solvents or column chromatography over silica gel.

The final step in the preferred reaction process used to prepare compounds of the invention involves reacting the halogen substituted-N-heterocyclic carboxylic acid amide intermediate with at least one equivalent of a suitable acid acceptor. Preferred acid acceptors are alkali metal carbonates, such as potassium carbonate and sodium carbonate; alkaline earth metal carbonates, such as barium carbonate and magnesium carbonate; alkaline earth metal hydroxides, such as barium hydroxide and magnesium hydroxide; and organic bases such as triethylamine, pyridine and 1,5-diazabicyclo[4.3.0]-non-5-ene(DBN). Preferred acid acceptors are the alkali metal hydroxides such as sodium hydroxide and potassium hydroxide. Preferred solvents for use in this reaction are the alcohols such as methanol or ethanol. The reaction is carried out in a temperature in the range of from about 10° C. to 150° C., more preferably from about 25° C. to the reflux temperature of the reaction mixture. The reaction mixture is then worked up according to standard procedures. Typically, the mixture is added to water and the product either collected by filtration or extracted into a water immiscible solvent such as toluene or dichloromethane. The product may then be further purified by standard procedures if desired.

The starting materials used to prepare compounds and intermediates of the present invention are either commercially available or readily prepared by known procedures. For example, certain halogen substituted carboxylic acid halide derivative starting materials are preferably prepared by reacting an acetyl lactone derivative with sodium alkoxide and an alkyl halide to provide the corresponding alkyl lactone, which is converted to the appropriate acid halide derivatives with a suitable halogenating agent and zinc chloride according to the following reaction scheme:

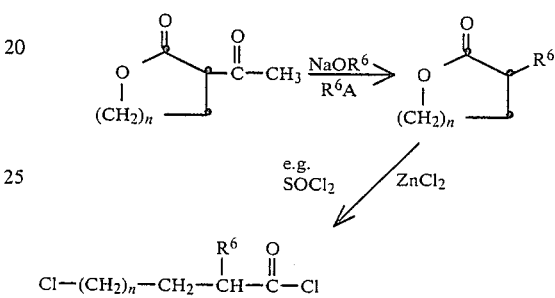

wherein n and A are as defined above and $R^6$ is $C_1$-$C_6$ alkyl.

The compounds of the present invention may also be conveniently prepared by reacting a lactam salt with a heterocycle according to the following scheme:

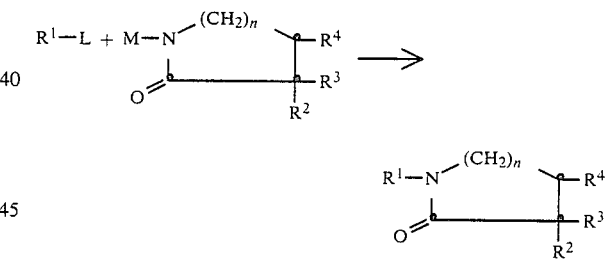

wherein $R^1$, $R^2$, $R^3$, $R^4$ and n are as defined above, M is a group IA or IIA metal and L is a leaving group.

This reaction is carried out under anhydrous conditions using any suitable inert solvent. The ethers such as diethyl ether, dioxane and tetrahydrofuran are particularly useful; however, solvents such as dimethylformamide (DMF), N-methylpyrrolidone and hexamethylphosphoric triamide may also be employed. The reaction is typically carried out at temperatures between 0° and 110° C., preferably between 0° and 40° C., most preferably at room temperature. The product has usually formed after about 1 to 6 hours. The product thus formed is then isolated and purified by procedures well known to those skilled in the art.

In the above reaction scheme a preferred lactam salt is a lithium derivative. Preferred leaving groups on the heterocyclic ring include halogen, more preferably chlorine, bromine and iodine.

The following Examples are illustrative of compounds and intermediates of the present invention.

These Examples are not intended to be limiting to the scope in any respect and should not be so construed.

EXAMPLE 1

1-[5-(1,1-Dimethylethyl)-3-isoxazolyl]-3-methyl-2-pyrrolidinone

A. 2-Methyl-4-chlorobutyric acid chloride

To a stirring solution of 77 g of α-methyl-γ-butyrolactone and 1 g of zinc chloride was added 120 g of thionyl chloride. The reaction was allowed to stir at room temperature for about 16 hours and then was heated to 75°–80° C. for 24 hours. The reaction mixture was distilled at 10 mm pressure to provide 2-methyl-4-chlorobutyric acid chloride. bp=57°–60° C.

B. 4-Chloro-N-[5-(1,1-dimethylethyl)-3-isoxazolyl]-2-methylbutanamide

To a stirred solution of 7 g of 3-amino-5-(1,1-dimethylethyl)isoxazole and 5.05 g triethylamine dissolved in 100 ml ethyl acetate was added 7.75 g of 2-methyl-4-chlorobutyric acid chloride dropwise. The mixture was stirred for about 16 hours at room temperature and the precipitated salt was collected by filtration and washed with ethyl acetate. The filtrate was concentrated under reduced pressure and the residue was chromatographed over silica gel while eluting with a 1:1 (v/v) mixture of toluene:diethyl ether. Fractions containing the major component as indicated by thin layer chromatography were combined and concentrated under vacuum to provide 7 g of 4-chloro-N-[5-(1,1-dimethylethyl)-3-isoxazolyl]-2-methylbutanamide. Yield 54%. This material was used in the following reaction without additional purification.

C. To a solution of 7 g of 4-chloro-N-[5-(1,1-dimethylethyl)-3-isoxazolyl]-2-methylbutanamide in 10 ml of ethanol was added 2 g of powdered potassium hydroxide in 5 ml water and 5 ml ethanol. The mixture was refluxed for 30 minutes, cooled and poured into 40 ml water. A gummy solid was collected by filtration and recrystallized from pentane to afford 1-[5-(1,1-dimethylethyl)-3-isoxazolyl]-3-methyl-2-pyrrolidinone as a solid. mp 89°–90° C.

Analysis calculated for $C_{12}H_{18}N_2O_2$: Theory: C, 64.84; H, 8.16; N, 12.60. Found: C, 64.57; H, 7.93; N, 12.78.

EXAMPLE 2

1-[3-(1,1-Dimethylethyl)-5-isoxazolyl]-3-methyl-2-pyrrolidinone

A. 4-Chloro-N-[3-(1,1-dimethylethyl)-5-isoxazolyl]-2-methylbutanamide

To a stirred solution of 7 g of 3-(1,1-dimethylethyl)-5-aminoisoxazole dissolved in 50 ml ethyl acetate was added 5.05 g of triethylamine at room temperature. As the solution continued to stir, 8 g of 2-methyl-4-chlorobutyric acid chloride was added to the reaction mixture over a 15 minute period. The reaction was allowed to stir for about 3 days and the precipitated triethylamine hydrochloride salt was collected by filtration and washed with ethyl acetate. The solvent was evaporated from the filtrate under reduced pressure and the residue was recrystallized from diethyl ether to afford 4-chloro-N-[3-(1,1-dimethylethyl)-5-isoxazolyl]-2-methylbutanamide as a solid. mp 135°–137° C.

Analysis calculated for $C_{12}H_{19}ClN_2O_2$: Theory: C, 55.70; H, 7.40; N, 10.83. Found: C, 55.41; H, 7.15; N, 10.84.

B. Two grams of 4-chloro-N-[3-(1,1-dimethylethyl)-5-isoxazolyl]-2-methylbutanamide was added by portion to a stirring solution of 0.6 g of powdered potassium hydroxide dissolved in 2 ml of water and 5 ml of ethanol. The reaction mixture was heated to reflux for 15 minutes, cooled and poured into 20 ml of water. The precipitated solid was collected by filtration to afford 1.5 g of 1-[3-(1,1-dimethylethyl)-5-isoxazolyl]-3-methyl-2-pyrrolidinone. Yield 87%. mp 73°–75° C.

Analysis calculated for $C_{12}H_{18}N_2O_2$: Theory: C, 64.84; H, 8.16; N, 12.60. Found: C, 64.65; H, 8.44; N, 12.46.

EXAMPLE 3

1-[3-(1,1-Dimethylethyl)-5-isothiazolyl]-3-methyl-2-pyrrolidinone

A. 4-Chloro-N-[3-(1,1-dimethylethyl)-5-isothiazolyl]-2-methylbutanamide

To a solution of 2.4 g of 3-(1,1-dimethylethyl)-5-aminoisothiazole dissolved in 150 ml of toluene under nitrogen was added 2.3 g of 2-methyl-4-chlorobutyric acid chloride. The reaction mixture was refluxed for about 24 hours and cooled. The solvent was evaporated under reduced pressure, and the product was isolated from the residue by chromatography over silica gel eluting with an ethyl acetate/Skellysolve B solvent mixture. Fractions containing the major component were combined and the solvent was evaporated therefrom to afford, following crystallization from toluene/Skellysolve B, 0.5 g of 4-chloro-N-[3-(1,1-dimethylethyl)-5-isothiazolyl]-2-methylbutanamide. Yield 12%. mp 144°–146° C.

Analysis calculated for $C_{12}H_{19}ClN_2OS$: Theory: C, 52.45; H, 6.97; N, 10.19. Found: C, 52.50; H, 6.69; N, 10.22.

B. To a stirred solution of 0.5 g of 4-chloro-N-[3-(1,1-dimethylethyl)-5-isothiazolyl]-2-methylbutanamide dissolved in 30 ml ethanol was slowly added 0.112 g of potassium hydroxide dissolved in ethanol/water. The mixture was stirred at room temperature for about one-half hour and poured into water. The solution was extracted with diethyl ether, and the organic phase was washed with water, filtered, dried, filtered again, and finally evaporated to dryness under reduced pressure. The product crystallized from Skellysolve B to provide about 0.2 g of 1-[3-(1,1-dimethylethyl)-5-isothiazolyl]-3-methyl-2-pyrrolidinone. Yield 46%. mp 111°–113° C.

NMR: multiplet at $\delta 1.4$ (15 protons); multiplet at $\delta 3.8$ (2 protons); and singlet at $\delta 6.6$ (1 proton).

EXAMPLE 4

1-[5-(1,1-Dimethylbutyl)-3-isoxazolyl]-3-methyl-2-pyrrolidinone was prepared by reacting 17.2 g of 4-chloro-N-[5-(1,1-dimethylbutyl)-3-isoxazolyl]-2-methylbutanamide with 6.72 g of potassium hydroxide in 30 ml water and 75 ml ethanol by the general method of Example 3. Weight 4 g (Yield 20%). mp 30°–31° C.

Analysis calculated for $C_{14}H_{22}N_2O_2$: Theory: C, 67.17; H, 8.86; N, 11.19. Found: C, 67.40; H, 8.62; N, 11.13.

The following examples further illustrate compounds of the invention and were prepared by the general procedures outlined above.

EXAMPLE 5

1-[5-(1,1-Dimethylethyl)-3-isoxazolyl]-2-pyrrolidinone mp 64° C.

Analysis calculated for $C_{11}H_{16}N_2O_2$: Theory: C, 63.46; H, 7.69; N, 13.46. Found: C, 63.17; H, 7.89; N, 13.66.

EXAMPLE 6

1-[5-(1,1-Dimethylethyl)-3-isoxazolyl]-3-methyl-2-piperidinone mp 43°–45° C.

Analysis calculated for $C_{13}H_{20}N_2O_2$: Theory: C, 66.07; H, 8.53; N, 11.85. Found: C, 66.31; H, 8.79; N, 11.57.

EXAMPLE 7

1-[5-(1-Methylethyl)-3-isoxazolyl]-3-methyl-2-pyrrolidinone mp 38°–40° C.

Analysis calculated for $C_{10}H_{16}N_2O_2$: Theory: C, 63.44; H, 7.74; N, 13.45. Found: C, 63.17; H, 7.80; N, 13.37.

EXAMPLE 8

1-[5-(1,1-Dimethylethyl)-1,2,4-oxadiazol-3-yl]-3-methyl-2-pyrrolidinone mp 84°–86° C.

Analysis calculated for $C_{10}H_{17}N_3O_2$: Theory: C, 59.17; H, 7.67; N, 18.82. Found: C, 58.93; H, 7.27; N, 18.62.

EXAMPLE 9

1-[5-(1-Ethyl-1-methylpropyl)-3-isoxazolyl]-3-methyl-2-pyrrolidinone oil

Analysis calculated for $C_{13}H_{22}N_2O_2$: Theory: C, 67.17; H, 8.86; N, 11.19. Found: C, 66.98; H, 8.65; N, 10.93.

EXAMPLE 10

1-[5-(1-Ethyl-1-methylpropyl)-1,3,4-oxadiazol-2-yl]-3-methyl-2-pyrrolidinone oil NMR: multiplet from δ0.9 to 2.0 (19 protons); and multiplet at δ4.1 (2 protons).

EXAMPLE 11

1-[5-(1,1,-Dimethylethyl)-3-isoxazolyl]-3-ethyl-2-pyrrolidinone oil

Analysis calculated for $C_{12}H_{20}N_2O_2$: Theory: C, 66.07; H, 8.53; N, 11.85. Found: C, 65.79; H, 8.44; N, 11.85.

EXAMPLE 12

1-[5-(1,1-Dimethylethyl)-3-isoxazolyl]hexahydro-2H-azepin-2-one mp 66°–68° C.

Analysis calculated for $C_{13}H_{20}N_2O_2$: Theory: C, 66.07; H, 8.53; N, 11.85. Found: C, 65.86; H, 8.25; N, 11.61.

EXAMPLE 13

1-[5-(1,1-Dimethylethyl)-3-isoxazolyl]-2-piperidinone mp 71°–72° C.

Analysis calculated for $C_{12}H_{18}N_2O_2$: Theory: C, 64.84; H, 8.16; N, 12.60. Found: C, 64.59; H, 7.91; N, 12.60.

EXAMPLE 14

1-[5-(1-Ethylcyclohexyl)-3-isoxazolyl]-3-methyl-2-pyrrolidinone mp 61°–63° C.

Analysis calculated for $C_{16}H_{24}N_2O_2$: Theory: C, 69.53; H, 8.75; N, 10.14. Found: C, 69.82; H, 8.50; N, 9.89.

EXAMPLE 15

1-[5-(1,1-Dimethylethyl)-3-isoxazolyl]-3,3-dimethyl-2-pyrrolidinone mp 123°–125° C.

Analysis calculated for $C_{12}H_{21}N_2O_2$: Theory: C, 66.07; H, 8.53; N, 11.85. Found: C, 65.87; H, 8.65; N, 11.87.

EXAMPLE 16

1-[5-(1,1-Dimethylethyl)-3-isoxazolyl]-3-bromo-2-pyrrolidinone mp 159°–161° C.

Analysis calculated for $C_{11}H_{15}BrN_2O_2$: Theory: C, 46.01; H, 5.27; N, 9.76. Found: C, 46.26; H, 5.37; N, 9.53.

The following compounds exemplify the intermediates contemplated as a further embodiment of the present invention.

EXAMPLE 17

4-Chloro-N-[5-(1,1-dimethylethyl)-3-isoxazolyl]-2-methylbutanamide mp 87°–89° C.

EXAMPLE 18

4-Chloro-N-[3-(1,1-dimethylethyl)-5-isoxazolyl]-2-methylbutanamide mp 135°–137° C.

Analysis calculated for $C_{12}H_{19}ClN_2O_2$: Theory: C, 55.70; H, 7.40; N, 10.83. Found: C, 55.41; H, 7.15; N, 10.84.

EXAMPLE 19

4-Chloro-N-[3-(1,1-dimethylethyl)-5-isothiazolyl]-2-methylbutanamide mp 144°–146° C.

Analysis calculated for $C_{12}H_{19}ClN_2OS$: Theory: C, 52.45; H, 6.97; N, 10.19. Found: C, 52.50; H, 6.69; N, 10.22.

EXAMPLE 20

4-Chloro-N-[5-(1,1-dimethylbutyl)-3-isoxazolyl]-2-methylbutanamide

EXAMPLE 21

4-Chloro-N-[5-(1,1-dimethylethyl)-3-isoxazolyl]butanamide mp 73°–75° C.

EXAMPLE 22

5-Iodo-N-[5-(1,1-dimethylethyl)-3-isoxazolyl]-2-methylpentanamide oil

EXAMPLE 23

4-Chloro-N-[5-(1-methylethyl)-3-isoxazolyl]-2-methylbutanamide mp 64°–66° C.

Analysis calculated for $C_{11}H_{17}ClN_2O_2$: Theory: C, 53.99; H, 7.00; N, 11.45. Found: C, 53.91; H, 7.04; N, 11.27.

EXAMPLE 24

4-Chloro-N-[5-(1,1-dimethylethyl)-1,2,4-oxadiazol-3-yl]-2-methylbutanamide mp 154°–156° C.

Analysis calculated for $C_{11}H_{18}ClN_3O_2$: Theory: C, 50.87; H, 6.99; N, 16.18. Found: C, 50.72; H, 6.99; N, 16.11.

EXAMPLE 25

4-Chloro-N-[5-(1-methyl-1-ethylpropyl)-3-isoxazolyl]-2-methylbutanamide mp 59°–61° C.

Analysis calculated for $C_{14}H_{23}ClN_2O_2$: Theory: C, 58.63; H, 8.08; N, 9.77. Found: C, 58.35; H, 7.87; N, 9.76.

EXAMPLE 26

4-Chloro-N-[5-(1,1-dimethylethyl)-3-isoxazolyl]-2-ethylbutanamide mp 74°–76° C.

EXAMPLE 27

6-Chloro-N-[5-(1,1-dimethylethyl)-3-isoxazolyl]hexanamide mp 81°–83° C.

Analysis calculated for $C_{13}H_{21}ClN_2O_2$: Theory: C, 57.24; H, 7.76; N, 10.27; Cl, 13.00. Found: C, 57.50; H, 7.85; N, 10.07; Cl, 13.07.

EXAMPLE 28

5-Chloro-N-[5-(1,1-dimethylethyl)-3-isoxazolyl]pentanamide mp 71°–73° C.

Analysis calculated for $C_{12}H_{19}ClN_2O_2$: Theory: C, 55.70; H, 7.40; N, 10.83. Found: C, 55.95; H, 7.36; N, 10.86.

EXAMPLE 29

4-Chloro-N-[5-(1,1-dimethylethyl)-3-isoxazolyl]-2,2-dimethylbutanamide mp 97°–99° C.

EXAMPLE 30

4-Chloro-N-[5-(1-ethylcyclohexyl)-3-isoxazolyl]-2-methylbutanamide oil

EXAMPLE 31

4-Bromo-N-[5-(1,1-dimethylethyl)-3-isoxazolyl]-2-methylbutanamide mp 94°–96.5° C.

Analysis calculated for $C_{12}H_{19}BrN_2O_2$: Theory: C, 47.54; H, 6.32; N, 9.24. Found: C, 47.89; H, 6.43; N, 9.07.

EXAMPLE 32

2,4-Dibromo-N-[5-(1,1-dimethylethyl)-3-isoxazolyl]butanamide mp 148°–150° C.

Analysis calculated for $C_{11}H_{16}Br_2N_2O_2$: Theory: C, 35.90; H, 4.38; N, 7.61. Found: C, 36.06; h, 4.48; n 7.36.

The compounds and intermediates of the present invention are useful both as preemergent and postemergent herbicides. Therefore, yet another embodiment of the invention is a method for controlling undesired plants which comprises applying to the plants, or the locus of the plants, a growth inhibiting amount of a present compound or intermediate.

The compounds and intermediates of the present invention display activity against a wide variety of weeds. Examples of typical weeds include, but are not limited to, the following:

Wild Oat (*Avena fatua*)
Catchweed Bedstraw (*Galium aparine*)
Scentless Mayweed (*Matricaria inodora*)
Ladysthumb (*Polygonum persicaria*)
Common Chickweed (*Stellaria media*)
Ivyleaf Speedwell (*Veronica hederaefolia*)
Blackgrass (*Alopecurus myosuroides*)
Chrysanthenum (Chrysanthenum spp.)
Common Purslane (*Portulaca oleracea*)
Sida (Sida spp.)
Bristly Starbur (*Acanthospermum hispidum*)
Goosegrass (*Eleusine indica*)
Smooth Pigweed (*Amaranthus hybridus*)
Alexandergrass (*Brachiaria plantaginea*)
Tall Morningglory (*Ipomoea purpurea*)
Common Lambsquarters (*Chenopodium album*)
Green Smartweed (*Polygonum scabrum*)
Green Foxtail (*Setaria viridis*)
Redroot Pigweed (*Amaranthus retroflexus*)
Morningglory Smartweed (*Polygonum convolvulus*)
Brazil Calalilly (*Richardia brasiliensis*)
Natal Grass (*Rhynchelytrum roseum*)
Ryegrass (*Lolium rigidum*)
Kapeweed (Cryptostemma calendula)
Purple Loosestrife (*Lythrum salicaria*)
Wild radish (*Raphanus raphanistrum*)
Wireweed (*Polygonum aviculare*)
Henbit (*Lamium amplexicaule*)
Wild Mustard (*Brassica kaber*)
Barnyardgrass (*Echinochloa crus-galli*)
Foxtail Millet (*Setaria italica*)
Velvetleaf (*Abutilon theophrasti*)
Indian Mustard (*Brassica juncea*)
Birdseye Speedwell (*Veronica persica*)
Canada Thistle (*Cirsium arvense*)
Wild Chamomile (*Matricaria chamomilla*)
Annual Bluegrass (*Poa annua*)
Buttercup (Ranunculus spp.)
Field Speedwell (*Veronica agrestis*)
Field Violet (*Viola arvensis*)
Field Pennycress (*Thlaspi arvense*)
Wild Violet (*Viola tricolor*)
Shirley Poppy (*Papaver rhoeas*)
Field Poppy (*Papaver dubium*)
Foolsparsley (*Aethusa cynapium*)
Field Chickweed (*Cerastium arvense*)
Southern Sanbur (*Cenchrus echinatus*)
Large Crabgrass (*Digitaria sanguinalis*)
Cheat (*Bromus secalinus*)

Morningglory (Ipomea spp.)
Common Ragweed (*Ambrosia artemisiifolia*)
Common Milkweed (*Asclepias syriaca*)
Giant Foxtail (*Setaria faberi*)
Common Cocklebur (*Xanthium pensylvanicum*)
Spurred Anoda (*Anoda cristata*)
Sicklepod (*Cassia obtusifolia*)
Yellow Nutsedge (*Cyperus esculentus*)
Jimsonweed (*Datura stramonium*)
Large Crabgrass (*Digitaria sanguinalis*)
Prickly Sida (*Sida spinosa*)
Corn Gromwell (*Lithospermum arvense*)
Yellow Foxtail (*Setaria glauca*)
Tansymustard (*Descurainia pinnata*)
Pepperweed (Lepidium spp.)
Bromegrass (Bromus spp.)
Garden Spurge (*Euphorbia hirta*)
Crowfootgrass (*Dactyloctenium aegyptium*)
Florida Beggarweed (*Desmodium tortuosum*)
Spotted Spurge (*Euphorbia maculata*)
Smallflower Morningglory (*Jacquemontia tamnifolia*)
Browntop Millet (*Panicum ramosum*)
Coast Fiddleneck (*Amsinckia intermedia*)
Wild Turnip (*Brassica campestris*)
Black Mustard (*Brassica nigra*)
Shepherdspurse (*Capsella bursa-pastoris*)
Italian Ryegrass (*Lolium multiflorum*)
London Rocket (*Sisymbrium irio*)
Redmaids Rockpurslane (*Calandrinia caulescens*)
Common Groundsel (*Senecio vulgaris*)
Ivyleaf Morningglory (*Ipomoea hederacea*)
Fall Panicum (*Panicum dichotomiflorum*)
Powell Amaranth (*Amaranthus powellii*)
Texas Panicum (*Panicum texanum*)
Hemp Sesbania (*Sesbania exaltata*)
Annual Sowthistle (*Sonchus oleraceus*)
Field Bindweed (*Convolvulus arvensis*)
Erect Knotweed (*Polygonum erectum*)
Venice Mallow (*Hibiscus trionum*)
Zinnia (*Zinnia elegans*)
Nightshade (Solanum spp.)

The present compounds and intermediates have also been found safe on a wide variety of desirable plant species, thereby exhibiting their unique selective capacity. Representative examples of relatively tolerant plant species, depending on the concentration of active employed, include the following:
Corn (*Zea mays*)
Wheat (*Triticum aestivum*)
Soybean (*Glycine max*)
Rice (*Oryza sativa*)
Barley (*Hordeum vulgare*)
Cotton (*Gossypium hirsutum*)
Sorghum (*Sorghum vulgare v. saccharatum*)
Sugarcane (*Saccharum officinarum*)
Peanut (*Arachis hypogaea*)
Peas (*Pisum sativum*)
Alfalfa (*Medicago sativa*)
Cucumber (*Cucumis sativus*)
Tomato (*Lycopersicon esculentum*)
Sugar beets (*Beta vulgaris*)
Cabbage (*Brassica oleracea capitata*)

The compounds of the present invention have been found to be particularly useful for the control of weeds in cereal grains, such as wheat, when applied either preemergence or postemergence to the locus.

The term "growth inhibiting amount", as defined herein, refers to an amount of a compound or intermediate of the present invention which either kills or stunts the growth of the weed species for which control is desired. This amount will generally be from about 0.05 to about 20.0 pounds or greater of a compound or intermediate of the invention per acre (about 0.056 to about 22.4 kg/ha). The compounds are more preferably applied at rates of about 0.10 to about 8.0 pounds per acre (about 0.112 to about 8.96 kg/ha), while the intermediates are more preferably applied at rates of about 0.20 to about 10.0 lbs/acre (about 0.224 to about 11.2 kg/ha). The exact concentration of active ingredient required varies with the weed species to be controlled, type of formulation, soil type, climate conditions and the like.

The term "undesired plants", as defined herein, refers to both weeds and weed seeds which are present at the location to be treated with an active agent of the present invention. These compounds and intermediates can be applied to the soil to selectively control undesired plants by soil contact when the weed seeds are germinating and emerging. They can also be used directly to kill emerged weeds by direct contact with the exposed portion of the weed.

The compounds and intermediates can also be used in the control of unwanted vegetation in non-crop land, for instance in a chemical fallow land program, particularly in fallow wheatland and the like.

Due to their unusually high activity, the present active agents can also be used non-selectively for total vegetation control when used in amounts generally greater than 10 lbs/acre (11.2 kg/ha).

The compounds and intermediates of the present invention are preferably formulated with a suitable agriculturally-acceptable carrier for ease of application. Such compositions will contain from about 0.1 to about 95.0 percent by weight of the active ingredient, depending on the composition desired. Examples of typical herbicidal compositions contemplated by the present invention include sprayable formulations, such as wettable powders, aqueous suspensions and emulsifiable concentrates; and solid compositions, such as dusts and granules.

The most convenient formulations are in the form of concentrated compositions to be applied by spraying as water dispersions or emulsions containing in the range from about 0.1 percent to about 10 percent of the active agent by weight. Water-dispersible or emulsifiable compositions may be either solids, usually known as wettable powders, or liquids, usually known as emulsifiable concentrates and aqueous suspensions.

A typical wettable powder comprises an intimate mixture of an active ingredient of the invention, an inert carrier, and surfactants. The concentration of the active agent is usually from about 25 percent to about 90 percent by weight. The inert carrier is usually chosen from among the attapulgite clays, the montmorillonite clays, the diatomaceous earths, or the purified silicates. Effective surfactants, comprising from about 0.5 percent to about 10 percent by weight of the wettable powder, are chosen from among the sulfonated lignins, the condensed napthalenesulfonates, and the alkyl sulfates.

A typical emulsifiable concentrate comprises from about 0.1 to about 6 pounds of a compound or intermediate of the invention per gallon of liquid (about 0.0112 to about 0.672 kg/l.), dissolved in a mixture of organic solvents and emulsifiers. The organic solvent is chosen with regard to its solvency and its cost. Useful solvents include the aromatics, especially the xylenes and the heavy aromatic naphthas. Hydrophilic cosolvents such as cyclohexanone and the glycol ethers such as 2-methoxyethanol may be included. Other organic solvents may also be used, including the terpenic solvents and kerosene. Suitable emulsifiers for emulsifiable concentrates are chosen from the alkylbenzenesulfonates, naphthalenesulfonates, and nonionic surfactants such as alkylphenol adducts of polyoxyethylene, and are used at similar percentages as for wettable powders.

An aqueous suspension, or flowable, is comprised of a finely ground suspension of the active ingredient dispersed in a water based system. This type of formulation is particularly useful for compounds with low water solubility. The concentration of active agent is usually from about 15 to 60 percent by weight. A typical aqueous suspension may comprise wetting and dispersing agents, antifreeze components, thickening or bulking agents as well as water and the active ingredient.

Dust compositions containing a compound or intermediate of the present invention usually contain from about 0.1 to about 10 percent by weight of the compound. Dusts are prepared by intimately mixing and finely grinding the active agent with an inert solid such as ground montmorillonite clay, attapulgite clay, talc, ground volcanic rock, kaolin clay, or other inert, relatively dense, inexpensive substances.

Solid, granular compositions are convenient for the application of compounds or intermediates of this invention to the soil and will contain the active agent in an amount from about 0.1 to about 20 percent by weight. Granules comprise a compound of the invention dispersed on a granular inert carrier such as coarsely ground clay of from about 0.1 to about 3 mm particle size. The active ingredient is most conveniently applied to the clay by dissolving it in an inexpensive solvent, such as acetone, and applying the solution to the sized clay in an appropriate solids mixer. The solvent is then typically removed by evaporation prior to applying the granules to the application site.

When operating in accordance with the present invention, the present compounds and intermediates, or compositions thereof, may be applied to the site where herbicidal or algicidal control is desired by any convenient manner, e.g., by means of hand dusters or sprayers. Metering applicators can apply accurately measured quantities of granular compositions to the locus to be treated. Other applications can be carried out with power dusters, boom sprayers, high-pressure sprayers and spray dusters. In large scale operations, dusts or low-volume sprays can be applied aerially, for example from airplanes or helicopters, to the application site. When applying the formulations described above, it is important to apply the desired concentration of active ingredient uniformly to the plants or locus to be treated.

The following examples provide an illustration of typical agriculturally-acceptable compositions comprehended by this invention.

| Wettable Powder | |
|---|---|
| Ingredient | Concentration by Weight (Percent) |
| 4-Chloro-N—[5-(1,1-dimethylethyl)-3-isoxazolyl]-2-methylbutanamide | 50.0 |
| Igepal, a nonionic wetting agent, GAF Corporation | 5.0 |
| Polyfon O, lignosulfonate dispersant, Westvaco Corporation | 5.0 |
| Zeolex 7, a precipitated hydrated silica bulking agent, J. M. Huber Corporation | 5.0 |
| Barden Clay, a kaolinite clay, J. M. Huber Corporation | 35.0 |
| | 100.0 |

The ingredients are combined and finely ground to provide a free-flowing powder that can be suspended in water for convenient spray application.

| Aqueous Suspension | |
|---|---|
| Ingredient | Concentration by Weight (Percent) |
| 1-[5-(1,1-Dimethylethyl)-3-isoxazolyl]-2-piperidinone | 45.0 |
| Polyfon H, an anionic lignosulfonate wetting agent and dispersant, Westvaco Corporation | 3.0 |
| Sponto 2174, an emulsifier, Witco Chemical Corporation | 4.0 |
| Ethylene Glycol | 8.0 |
| Xanthum Gum thickening agent | 0.2 |
| Antifoam C foam suppressant, Dow Corning Corporation | 0.5 |
| Water | 39.3 |
| | 100.0 |

The above ingredients are intimately admixed and finely ground to provide a suitable suspension, which is then further diluted with water at the application site.

| Dust | |
|---|---|
| Ingredient | Concentration by Weight (Percent) |
| 1-[3-(1,1-Dimethylethyl)-5-isoxazolyl]-3-methyl-2-piperidinone | 10.0 |
| Diatomite, a diatomaceous earth, Witco Chemical Corporation, Inorganic Specialties Division | 90.0 |
| | 100.0 |

The active ingredient and diatomaceous earth are intimately mixed and ground to a fine powder of uniform particle size of about 16 to about 40 microns. The dust thus formed may be applied by any number of conventional methods, for example by an aerial application.

| Granules | |
|---|---|
| Ingredient | Concentration by Weight (Percent) |
| 1-[5-(1,1-Dimethylethyl)-3-isoxazolyl]-3-methyl-2-pyrrolidinone | 5.0 |
| Heavy aromatic naphtha | 5.0 |
| Bentonite 20/40 mesh granular clay, The Floridin Company | 90.0 |
| | 100.0 |

The compound is dissolved in the naphtha and sprayed onto the clay granules, typically under agitation, and the formulated granules are sieved to provide a uniform mesh size.

The herbicidal activity of representative compounds and intermediates of the present invention is illustrated by the following experiments.

EXPERIMENT 1

The initial screen used to evaluate herbicidal efficacy was conducted at a test compound concentration of 15 lgs/acre (16.8 kg/ha). In this test a standard sand:soil mixture (1:1) was sterilized and added to separate containers and tomato, large crabgrass and pigweed seeds were planted by row. Each container was then fertilized before treatment.

The test compounds were formulated for application by dissolving the compound into a solvent prepared by combining Toximul R and Toximul S (proprietary blends of anionic and nonionic surfactants manufactured by Stepan Chemical Company, Northfield, Ill.) with a 1:1 (v/v) mixture of acetone:ethanol. The solvent/compound solution was diluted with deionized water and applied postemergence to some planted containers and preemergence to others using a DeVilbiss atomizer. Postemergence treatment was made 11 to 13 days after planting while preemergence treatment was made one day after planting.

Following treatment the containers were moved to the greenhouse and watered as necessary. Observations were made 10 to 13 days after treatment using untreated control plants as standards. The degree of herbicidal activity was determined by rating the treated plants on a scale of 1 to 5. On this scale "1" indicates no injury, "2" is slight injury, "3" is moderate injury, "4" is severe injury and "5" indicates death to the plant or no seedling emergence. Also, the various types of injury of each test species were coded as follows.

A = abscission of leaves
B = burned
C = chlorosis
D = death
E = epinasty
F = formation effects
G × dark green
I × increased plant growth
L = local necrosis
N = no germination
P = purple pigmentation
R = reduced germination
S = stunting
U = unclassified injury Table I presents the herbicidal activity of typical pyrrolidinone and haloamide derivatives of the invention when evaluated in the screen described above.

TABLE I

| | Herbicide Pretest at 15 lbs/acre (16.8 kg/ha) | | | | | |
|---|---|---|---|---|---|---|
| | Preemergence | | | Postemergence | | |
| Example No. of Compound Tested | Tomato | Large Crab-grass | Pig-weed | Tomato | Large Crab-grass | Pig-weed |
| 1 | 4CBS | 3S | 4BS | 5D | 5D | 5D |
| 2 | 3CS | 4RS | 4RS | 5D | 4BS | 5D |
| 4 | 3FS | 4RS | 4RS | 5D | 5D | 5D |
| 10 | 1 | 1 | 1 | 5D | 4BS | 5D |
| 23 | 1 | 2RS | 1 | 5D | 4BS | 5D |
| 28 | 1 | 1 | 1 | 1 | 5D | 5D |
| 32 | 1 | 1 | 1 | 1 | 1 | 1 |

EXPERIMENT 2

The herbicidal activity of some of the compounds and intermediates of the present invention was further evaluated at various application rates in a multiple species greenhouse test. Several additional weed and crop species were utilized to determine the herbicidal activity and selectivity of the test compounds. Lower concentrations of the test compounds were obtained by serial dilution of the above described formulation with a mixture of the surfactant containing solvent and deionized water. The compounds were evaluated according to the general procedure outlined above. Table II presents the preemergence herbicidal test results, while Table III presents postemergence test data administered at 8 lbs/acre (8.96 kg/ha) or less.

TABLE II

Preemergence

| Example No. of Compound Tested | Rate of Appln. lbs/acre (kg/ha) | Crops | | | | | | | | Weeds | | | | | | | | | |
|---|---|---|---|---|---|---|---|---|---|---|---|---|---|---|---|---|---|---|---|
| | | Corn | Cotton | Soybean | Wheat | Alfalfa | Sugar Beet | Rice | Cucumber | Tomato | Barnyard Grass | Lambsquarter | Large Crabgrass | Mustard | Pigweed | Foxtail | Wild Oat | Velvetleaf | Jimsonweed | Morningglory | Zinnia |
| 1 | 8.0 (8.96) | 5 | 3 | 4 | 5 | 5 | 5 | 3 | 5 | 5 | 4 | 5 | 5 | 5 | 5 | 5 | 5 | 5 | — | 5 | 5 |
| | 3.0 (3.36) | 2 | 2 | 3 | 4 | 5 | 5 | 2 | 5 | 5 | 4 | 5 | 4 | 5 | 5 | 5 | 5 | 5 | 4 | 3 | 5 |
| | 2.0 (2.24) | 2 | 2 | 3 | 4 | 5 | 4 | 2 | 5 | 5 | 3 | 4 | 4 | 5 | 4 | 5 | 3 | 5 | 4 | 3 | 5 |
| | 1.0 (1.12) | 2 | 2 | 1 | 2 | 5 | 4 | 2 | 5 | 5 | 1 | 4 | 4 | 4 | 3 | 3 | 3 | 5 | 4 | 3 | 5 |
| | 1.0 (1.12) | 1 | 1 | 1 | 1 | 5 | 5 | 1 | 3 | 3 | 1 | 4 | 3 | 4 | 3 | 3 | 1 | 5 | 3 | 2 | 4 |
| | 0.5 (0.56) | 1 | 1 | 1 | 2 | 3 | 3 | — | 2 | 2 | — | 4 | 3 | 3 | 3 | 3 | 1 | 4 | 3 | 2 | 4 |
| | 0.25 (0.28) | 1 | 1 | — | 1 | 1 | 3 | 2 | 2 | 2 | — | — | 1 | — | 1 | 2 | 1 | 2 | 2 | 2 | 4 |
| | 0.25 (0.28) | 1 | 1 | — | 1 | — | 2 | 1 | 2 | 2 | 3 | — | 3 | — | — | 2 | — | 2 | 1 | — | 2 |
| | 0.125 (0.14) | 1 | — | — | 1 | 2 | 2 | 2 | 1 | 1 | — | — | 1 | — | 1 | 1 | — | 1 | — | 1 | 1 |
| | 0.05 (0.056) | — | — | — | 1 | 1 | 1 | — | 1 | 1 | — | 1 | 1 | — | 1 | 1 | — | 2 | 1 | 1 | 1 |
| 2 | 8.0 (8.96) | 3 | 1 | 1 | — | — | 4 | — | 5 | 3 | — | — | 4 | — | 5 | 4 | — | 5 | — | 5 | 5 |
| | 4.0 (4.48) | 2 | 2 | 2 | 2 | 5 | 4 | 2 | 5 | 3 | 2 | 4 | 4 | 4 | 4 | 4 | 4 | 5 | 5 | 4 | 4 |
| | 2.0 (2.24) | 2 | 2 | 1 | 1 | 4 | 4 | 2 | 5 | 2 | 1 | 5 | 4 | 3 | 3 | 3 | 2 | 4 | 3 | 3 | 3 |
| | 1.0 (1.12) | 2 | 2 | 2 | 1 | 2 | 3 | 1 | 5 | 2 | 1 | — | 2 | 2 | 2 | 2 | 1 | 3 | 3 | 2 | 3 |
| | 1.0 (1.12) | 2 | 2 | 2 | 1 | 5 | 5 | 2 | 5 | 2 | 1 | 5 | — | 2 | 3 | 3 | 2 | 3 | 2 | 2 | 3 |
| | 0.5 (0.56) | 1 | 1 | — | — | 1 | 2 | 2 | 2 | 1 | — | — | — | 1 | 2 | 2 | 1 | 2 | — | — | 1 |
| | 0.25 (0.28) | 1 | 1 | — | — | 2 | 3 | 2 | 2 | 2 | — | 1 | 2 | — | 3 | 2 | 1 | 2 | 1 | — | 1 |
| 3 | 1.0 (1.12) | 3 | — | — | — | — | — | — | — | — | — | — | — | — | — | — | — | — | — | — | — |
| 4 | 8.0 (8.96) | 1 | 1 | — | 3 | 5 | 4 | 2 | 4 | 2 | 2 | 5 | 4 | 3 | 4 | 5 | 2 | 5 | — | 5 | 5 |
| | 4.0 (4.48) | 1 | 1 | — | 1 | 3 | 3 | 1 | 3 | — | 1 | 4 | 3 | — | 4 | 3 | — | 5 | 2 | 1 | 4 |
| | 2.0 (2.24) | 1 | 1 | — | 2 | 2 | 3 | 2 | 2 | — | 1 | 4 | 3 | 3 | 3 | 3 | 1 | 4 | 2 | 1 | 3 |
| | 1.0 (1.12) | 1 | 1 | 2 | 2 | 3 | 4 | — | 2 | 2 | 2 | 2 | 2 | 2 | 2 | 3 | 2 | 3 | 2 | 1 | 3 |
| | 1.0 (1.12) | 2 | 1 | — | 1 | 1 | 1 | 2 | 1 | 1 | — | — | — | 1 | 2 | 1 | 2 | 2 | — | — | 2 |
| | 0.5 (0.56) | — | — | — | 1 | 1 | 1 | — | — | — | — | — | 1 | — | 2 | 1 | — | 2 | — | 1 | — |
| | 0.25 (0.28) | — | — | — | 1 | 2 | — | — | 1 | 1 | — | — | 1 | — | 2 | 1 | — | 1 | — | 1 | 1 |
| 5 | 8.0 (8.96) | 3 | 3 | 3 | 4 | 5 | 5 | 2 | 5 | 5 | 4 | 5 | 5 | 5 | 5 | 5 | 4 | 5 | 4 | 2 | 5 |
| | 4.0 (4.48) | 1 | 3 | 4 | 2 | 3 | 3 | 2 | 5 | 4 | 2 | 4 | 5 | 5 | 4 | 5 | 5 | 5 | 4 | 1 | 5 |
| | 2.0 (2.24) | 1 | 1 | 2 | 2 | 2 | 4 | 2 | 3 | 2 | 2 | 4 | 4 | 4 | 4 | 3 | 4 | 5 | 3 | — | 4 |
| | 1.0 (1.12) | — | — | — | — | 1 | 2 | — | 2 | 2 | 1 | — | 2 | 2 | 2 | 1 | 2 | 4 | — | 1 | 2 |
| 6 | 8.0 (8.96) | 2 | 2 | 2 | 1 | 3 | 5 | 2 | 5 | 2 | 2 | 5 | 5 | 4 | 5 | 4 | 4 | 5 | 2 | 2 | 5 |
| | 4.0 (4.48) | 1 | 1 | 1 | 1 | 3 | 3 | 2 | 5 | 2 | 2 | 4 | 4 | 4 | 5 | 5 | 3 | 5 | 2 | 1 | 4 |
| | 2.0 (2.24) | 1 | 1 | 1 | 1 | 2 | 2 | 2 | 3 | 2 | 2 | 3 | 2 | 2 | 4 | 2 | 1 | 4 | 2 | — | 3 |
| | 1.0 (1.12) | 1 | 1 | — | 1 | 3 | 2 | 1 | 3 | — | 2 | 2 | 2 | 2 | 4 | 3 | — | 4 | 2 | 1 | 2 |
| 7 | 8.0 (8.96) | 2 | 2 | 2 | 1 | 3 | 5 | 2 | 5 | 2 | 2 | 5 | 5 | 4 | 5 | 4 | 4 | 5 | 2 | 2 | 5 |
| | 4.0 (4.48) | 1 | 1 | 1 | 1 | 3 | 4 | 2 | 5 | 3 | 2 | 4 | 4 | 2 | 3 | 3 | 2 | 4 | 2 | 1 | 4 |
| | 2.0 (2.24) | — | — | — | 1 | 2 | 3 | — | 5 | 3 | 2 | 3 | 3 | 3 | 2 | 2 | 1 | 4 | 2 | 1 | 3 |
| | 1.0 (1.12) | — | — | — | 1 | 3 | 2 | 1 | 4 | — | 2 | 4 | 3 | 2 | 2 | 1 | 1 | 3 | 1 | 1 | 3 |
| | 1.0 (1.12) | 1 | 1 | — | 1 | 1 | 2 | — | 2 | 2 | — | 3 | 2 | 3 | 2 | 2 | 1 | 3 | — | 1 | 2 |
| | 0.5 (0.56) | 1 | — | — | — | 1 | 2 | — | 2 | — | — | 2 | 1 | 2 | 2 | 1 | — | 3 | 1 | — | 2 |
| | 0.25 (0.28) | — | — | — | — | — | 1 | — | 1 | — | — | 2 | 1 | — | 1 | — | — | 2 | — | — | 2 |
| 8 | 8.0 (8.96) | 2 | 3 | 2 | 2 | 5 | 4 | 2 | 5 | 5 | 3 | 5 | 5 | 4 | 5 | 5 | 3 | 5 | 4 | 5 | 5 |
| | 4.0 (4.48) | 2 | 3 | 2 | 2 | 3 | 4 | 2 | 5 | 5 | 3 | 5 | 5 | 4 | 5 | 3 | 4 | 4 | 4 | 5 | 4 |
| | 4.0 (4.48) | 2 | 3 | 3 | 3 | 4 | 3 | 2 | 4 | 3 | 2 | 4 | 5 | 3 | 3 | 3 | 4 | 4 | 3 | 5 | 3 |
| | 2.0 (2.24) | 2 | 2 | 2 | 1 | 3 | 3 | 2 | 3 | 3 | 2 | 3 | 5 | 4 | 5 | 3 | 2 | 4 | 2 | 3 | 3 |
| | 1.0 (1.12) | 1 | 1 | 1 | 1 | 3 | 2 | 1 | 3 | 3 | 2 | 2 | 4 | 4 | 5 | 2 | 1 | 4 | 2 | 4 | 2 |
| | 1.0 (1.12) | — | 1 | — | — | 2 | 2 | 2 | 2 | 2 | 1 | 2 | 4 | 4 | 4 | 2 | — | 4 | 2 | 2 | 2 |
| | 0.5 (0.56) | 1 | — | — | — | 2 | 2 | 2 | 2 | 3 | — | 4 | 3 | 3 | 5 | 2 | — | 4 | 2 | 2 | 1 |

TABLE II-continued

Preemergence

| Example No. of Compound Tested | Rate of Appln. lbs/acre (kg/ha) | Crops | | | | | | | | | Weeds | | | | | | | | |
|---|---|---|---|---|---|---|---|---|---|---|---|---|---|---|---|---|---|---|---|
| | | Corn | Cotton | Soy-bean | Wheat | Alfalfa | Sugar Beet | Rice | Cu-cumber | Tomato | Barnyard Grass | Lambs-quarter | Large Crab-grass | Mustard | Pig-weed | Fox-tail | Wild Oat | Velvet-leaf | Jimson-weed | Morning-glory | Zinnia |
| 9 | 0.25 (0.28) | 1 | | | | | | | | | | | 2 | 1 | 1 | 2 | | 4 | 2 | 1 | 1 |
| | 8.0 (8.96) | | 4 | 2 | 2 | 4 | 4 | 1 | 5 | 5 | 4 | 5 | 5 | 5 | 5 | 4 | 3 | 5 | | 3 | 5 |
| | 4.0 (4.48) | 1 | 1 | 1 | 1 | 2 | 4 | | 5 | 4 | 4 | 5 | 4 | 4 | 4 | 4 | 2 | 5 | | 4 | 3 |
| | 2.0 (2.24) | 2 | 1 | 1 | | 1 | 1 | 1 | 1 | 1 | 1 | 4 | 4 | 2 | 3 | 3 | 1 | 5 | 2 | 1 | 1 |
| | 1.0 (1.12) | 1 | 1 | 1 | 1 | 1 | 1 | 1 | 1 | 1 | 1 | 3 | 4 | 2 | 3 | 2 | 1 | 5 | 2 | 1 | 1 |
| | 1.0 (1.12) | 1 | 1 | 1 | 1 | 1 | 1 | 1 | 1 | 1 | 1 | 3 | 1 | 1 | 1 | 1 | 1 | 2 | 1 | 1 | 1 |
| | 0.5 (0.56) | 1 | 1 | | | 1 | 1 | 1 | 1 | 1 | 1 | 2 | 1 | 1 | 1 | 1 | 1 | 1 | | 1 | 1 |
| | 0.25 (0.28) | 1 | | | | | | | | | | 1 | 1 | 1 | 1 | 1 | 1 | 1 | | 1 | 1 |
| 10 | 8.0 (8.96) | | | | | | 3 | 2 | 2 | 2 | 1 | 2 | 2 | 2 | 2 | 3 | 2 | 2 | 2 | 2 | 2 |
| 11 | 8.0 (8.96) | 1 | 1 | 1 | | 2 | 3 | 2 | 3 | 2 | 1 | 3 | 3 | 3 | 4 | 3 | 1 | 4 | 2 | 2 | 3 |
| | 4.0 (4.48) | | | | 1 | 1 | 1 | 2 | 2 | 2 | 1 | 2 | 2 | 2 | 4 | 3 | 2 | 4 | 1 | 2 | 2 |
| | 2.0 (2.24) | 1 | | 1 | 1 | 1 | 1 | 1 | 1 | | 1 | 2 | 2 | 2 | 2 | 3 | 1 | 2 | | | 3 |
| | 1.0 (1.12) | 1 | | | | | | | | | | 2 | | 2 | 3 | 2 | 1 | 2 | | | 2 |
| 12 | 8.0 (8.96) | | | | | | | | | | | | | | 3 | 1 | | | | | 1 |
| 13 | 8.0 (8.96) | 2 | 2 | 3 | 3 | 5 | 5 | 2 | 5 | 3 | 3 | 5 | 4 | 4 | 4 | 4 | 4 | 4 | 3 | 3 | 4 |
| | 4.0 (4.48) | 2 | 2 | 2 | 3 | 5 | 4 | 2 | 4 | 2 | 2 | 4 | 4 | 5 | 3 | 3 | 4 | 4 | 2 | 3 | 4 |
| | 2.0 (2.24) | 1 | 1 | 2 | 2 | 2 | 2 | 2 | 4 | 1 | 1 | 4 | 4 | 4 | 3 | 3 | 3 | 4 | 2 | 3 | 4 |
| | 1.0 (1.12) | 1 | | | | | | | | | | 1 | | 4 | 1 | 1 | 2 | 4 | | 1 | 2 |
| 14 | 8.0 (8.96) | | | | 2 | 5 | 4 | 2 | 5 | 4 | 2 | 5 | 4 | 4 | 5 | 5 | 5 | 5 | 2 | 5 | 5 |
| 15 | 8.0 (8.96) | 1 | 1 | 2 | 1 | 3 | 4 | 2 | 5 | 3 | 1 | 4 | 3 | 2 | 4 | 3 | 2 | 4 | 1 | 4 | 4 |
| | 4.0 (4.48) | 1 | 1 | 1 | 1 | 3 | 4 | 2 | 5 | 1 | 1 | 3 | 2 | 3 | 3 | 2 | 1 | 3 | 1 | 2 | 4 |
| | 2.0 (2.24) | | | | 1 | 3 | 2 | 1 | 2 | 2 | 2 | 2 | 2 | 2 | 2 | 2 | 1 | 3 | 1 | 3 | 2 |
| | 1.0 (1.12) | | | | | | | | | | | 1 | | 1 | 1 | 1 | | 1 | | 2 | 1 |
| 16 | 8.0 (8.96) | 1 | | | | | | | | 2 | | | | 3 | | 5 | | 5 | | 2 | 5 |
| 17 | 8.0 (8.96) | 1 | 3 | 2 | 2 | 5 | 5 | 3 | 5 | 5 | 4 | 5 | 5 | 5 | 5 | 5 | 5 | 5 | 5 | 5 | 5 |
| | 4.0 (4.48) | 1 | 2 | 1 | 1 | 5 | 5 | 2 | 5 | 5 | 1 | 5 | 4 | 2 | 4 | 5 | 4 | 5 | 4 | 3 | 3 |
| | 2.0 (2.24) | 1 | 1 | 1 | 1 | 3 | 4 | 1 | 4 | 1 | 1 | 4 | 4 | 3 | 4 | 4 | 1 | 4 | 3 | 2 | 2 |
| | 1.0 (1.12) | 1 | 1 | 1 | 1 | 3 | 3 | 1 | 1 | 1 | 1 | 2 | 2 | 2 | 3 | 1 | 1 | 3 | 1 | 2 | 1 |
| | 1.0 (1.12) | 1 | 1 | 1 | 1 | 4 | 4 | 1 | 1 | 1 | 1 | 2 | 3 | 1 | 2 | 1 | 2 | 5 | 1 | 3 | 2 |
| | 0.5 (0.56) | | | | | 1 | 3 | | | | | 1 | | | 1 | | | 1 | | 1 | 1 |
| | 0.25 (0.28) | 2 | | | | | | | | | | | | 3 | | | | | | 4 | 5 |
| 18 | 8.0 (8.96) | 3 | 2 | 2 | 1 | 4 | 4 | 2 | 5 | 4 | 2 | 4 | 3 | 3 | 4 | 3 | 1 | 5 | 3 | 4 | 3 |
| | 4.0 (4.48) | 1 | 2 | | 1 | 4 | 4 | 2 | 3 | 1 | 1 | 3 | 2 | 3 | 2 | 2 | 1 | 4 | 3 | 4 | 2 |
| | 2.0 (2.24) | 1 | 2 | 2 | 1 | 1 | 3 | 2 | 3 | 1 | 1 | 2 | 2 | 3 | 2 | 2 | 1 | 3 | 3 | 3 | 1 |
| | 1.0 (1.12) | | | | | | | | | 1 | | 1 | | 2 | 5 | 2 | 2 | 2 | | 1 | 2 |
| 19 | 8.0 (8.96) | | | | | | 4 | 2 | 5 | 5 | | 2 | 5 | 4 | 5 | 5 | 4 | 5 | | 5 | 5 |
| 31 | 8.0 (8.96) | 2 | 4 | 4 | 3 | 5 | 4 | 2 | 5 | 5 | 2 | 5 | 4 | 5 | 5 | 4 | 4 | 5 | 5 | 5 | 5 |
| | 2.0 (2.24) | 3 | 4 | 3 | 1 | 4 | 4 | 2 | 5 | 4 | 2 | 5 | 4 | 4 | 5 | 4 | 4 | 5 | 4 | 5 | 3 |
| | 1.0 (1.12) | 1 | 4 | 4 | 2 | 2 | 4 | 2 | 5 | 4 | 1 | 3 | 3 | 3 | 4 | 2 | 2 | 4 | 3 | 3 | 3 |
| | 0.5 (0.56) | | 2 | | | | | | | | | | | | | | | | 4 | | | |

TABLE III

Postemergence

| Example No. of Compound Tested | Rate of Appln. lbs/acre (kg/ha) | Corn | Tomato | Large Crabgrass | Pigweed | Foxtail | Velvetleaf | Morningglory | Zinnia | Barnyardgrass | Mustard | Wildoat |
|---|---|---|---|---|---|---|---|---|---|---|---|---|
| 1 | 8.0 (8.96) | 5 | | 4 | 5 | 3 | 5 | 4 | 4 | | | |
| | 3.0 (3.36) | 5 | | 4 | 5 | 5 | 5 | 4 | 5 | | | |
| | 2.0 (2.24) | 3 | | 2 | 4 | 2 | 3 | 3 | 4 | | | |
| | 1.0 (1.12) | 2 | | 2 | 4 | 3 | 3 | 3 | 3 | | | |
| 2 | 8.0 (8.96) | 1 | | 3 | 2 | 4 | 5 | 4 | 5 | | | |
| | 4.0 (4.48) | 1 | | 3 | 4 | 2 | 2 | 3 | 3 | | | |
| | 2.0 (2.24) | 1 | | 3 | 3 | 2 | 2 | 2 | 3 | | | |
| | 1.0 (1.12) | 1 | | 2 | 4 | 1 | 1 | 2 | 2 | | | |
| 3 | 1.0 (1.12) | | 1 | 1 | 1 | 2 | 1 | 2 | 2 | 1 | 2 | 1 |
| 4 | 8.0 (8.96) | 5 | | 5 | 5 | 5 | 5 | 4 | 5 | | | |
| | 4.0 (4.48) | 3 | | 4 | 4 | 3 | 5 | 3 | 4 | | | |
| | 2.0 (2.24) | 3 | | 4 | 4 | 2 | 4 | 2 | 4 | | | |
| | 1.0 (1.12) | 1 | | 2 | 2 | 2 | 5 | 1 | 3 | | | |
| | 1.0 (1.12) | 2 | | 2 | 2 | 3 | 5 | 2 | 4 | | | |
| | 0.5 (0.56) | 1 | | 1 | 1 | 2 | 4 | 1 | 3 | | | |
| | 0.25 (0.28) | 2 | | 1 | 1 | 1 | 1 | 1 | 1 | 3 | 1 | 1 |
| 5 | 8.0 (8.96) | 1 | | 4 | 5 | 2 | 5 | 3 | 3 | | | |
| | 4.0 (4.48) | 1 | | 3 | 3 | 2 | 3 | 2 | 2 | | | |
| | 2.0 (2.24) | 1 | | 1 | 1 | 2 | 1 | 1 | 2 | | | |
| | 1.0 (1.12) | 1 | | 1 | 1 | 1 | 1 | 1 | 1 | | | |
| 6 | 8.0 (8.96) | | 5 | 5 | 5 | 5 | 5 | 4 | 5 | 4 | 5 | 5 |
| | 4.0 (4.48) | | 3 | 5 | 3 | 4 | 5 | 3 | 5 | 2 | 4 | 4 |
| | 2.0 (2.24) | | 2 | 5 | 4 | 3 | 4 | 3 | 5 | 1 | 4 | 4 |
| | 1.0 (1.12) | | 1 | 4 | 3 | 3 | 3 | 2 | 4 | 1 | 3 | 3 |
| 7 | 8.0 (8.96) | | 4 | 4 | 5 | 4 | 5 | 4 | 5 | 2 | 5 | 2 |
| | 4.0 (4.48) | | 4 | 4 | 5 | 4 | 5 | 4 | 4 | 2 | 4 | 2 |
| | 2.0 (2.24) | | 2 | 3 | 4 | 3 | 4 | 4 | 4 | 2 | 4 | 1 |
| | 1.0 (1.12) | | 2 | 2 | 3 | 3 | 3 | 3 | 3 | 2 | 4 | 1 |
| 8 | 8.0 (8.96) | | 4 | 4 | 4 | 4 | 5 | 4 | 4 | 2 | 4 | 2 |
| | 4.0 (4.48) | | 4 | 4 | 5 | 3 | 4 | 4 | 4 | 2 | 4 | 2 |
| | 2.0 (2.24) | | 4 | 4 | 4 | 4 | 5 | 3 | 3 | 1 | 4 | 1 |
| | 1.0 (1.12) | | 3 | 2 | 2 | 1 | 3 | 3 | 2 | 1 | 4 | 1 |
| 9 | 8.0 (8.96) | | 5 | 5 | 5 | 5 | 5 | 5 | 5 | 3 | 5 | 5 |
| | 4.0 (4.48) | | 4 | 5 | 4 | 5 | 5 | 5 | 5 | 3 | 5 | 4 |
| | 2.0 (2.24) | | 4 | 5 | 5 | 4 | 5 | 4 | 5 | 3 | 5 | 4 |
| | 1.0 (1.12) | | 3 | 4 | 3 | 3 | 4 | 4 | 5 | 1 | 4 | 2 |
| | 1.0 (1.12) | | 1 | 2 | 2 | 2 | 3 | 4 | 2 | 1 | 2 | 1 |
| | 0.5 (0.56) | | 2 | 2 | 1 | 1 | 1 | 1 | 1 | 1 | 1 | 1 |
| | 0.25 (0.28) | | 1 | 1 | 1 | 1 | 1 | 1 | 1 | 1 | 1 | 1 |
| 10 | 8.0 (8.96) | | 2 | 3 | 2 | 3 | 3 | 2 | 2 | 1 | 2 | 2 |
| 11 | 8.0 (8.96) | | 5 | 5 | 5 | 4 | 4 | 4 | 4 | 1 | 5 | 2 |
| | 4.0 (4.48) | | 4 | 4 | 4 | 3 | 4 | 2 | 3 | 1 | 4 | 1 |
| | 2.0 (2.24) | | 4 | 4 | 4 | 4 | 2 | 3 | 3 | 2 | 4 | 2 |
| | 1.0 (1.12) | | 1 | 1 | 1 | 2 | 1 | 1 | 1 | 1 | 1 | 1 |
| 12 | 8.0 (8.96) | | 2 | 4 | 3 | 1 | 2 | 2 | 2 | 2 | 4 | 1 |
| 13 | 8.0 (8.96) | | 5 | 5 | 5 | 5 | 5 | 5 | 5 | 4 | 5 | 4 |
| | 4.0 (4.48) | | 4 | 5 | 5 | 4 | 5 | 3 | 5 | 3 | 5 | 3 |
| | 2.0 (2.24) | | 2 | 5 | 5 | 4 | 5 | 2 | 4 | 3 | 4 | 2 |
| | 1.0 (1.12) | | 2 | 4 | 4 | 3 | 4 | 2 | 2 | 1 | 4 | 1 |
| 14 | 8.0 (8.96) | | 4 | 4 | 3 | 3 | 5 | 4 | 3 | 2 | 5 | 3 |
| 15 | 8.0 (8.96) | | 4 | 4 | 4 | 3 | 4 | 4 | 4 | 2 | 4 | 2 |
| | 4.0 (4.48) | | 4 | 4 | 3 | 3 | 4 | 5 | 3 | 1 | 4 | 2 |
| | 2.0 (2.24) | | 3 | 2 | 2 | 2 | 3 | 5 | 3 | 1 | 4 | 1 |
| | 1.0 (1.12) | | 1 | 1 | 2 | 1 | 3 | 4 | 2 | 1 | 3 | 1 |
| 16 | 8.0 (8.96) | | 1 | 1 | 1 | 1 | 1 | 1 | 1 | 1 | 2 | 1 |
| 17 | 8.0 (8.96) | 2 | | 4 | 5 | 5 | 5 | 4 | 4 | | | |
| | 4.0 (4.48) | 3 | | 5 | 5 | 5 | 5 | 5 | 5 | | | |
| | 2.0 (2.24) | 3 | | 4 | 5 | 4 | 5 | 4 | 3 | | | |
| | 1.0 (1.12) | 1 | | 4 | 5 | 4 | 4 | 4 | 5 | | | |
| | 1.0 (1.12) | 3 | | 3 | 4 | 4 | 5 | 4 | 4 | | | |
| | 0.5 (0.56) | 1 | | 3 | 3 | 4 | 4 | 3 | 4 | | | |
| | 0.25 (0.28) | 1 | | 2 | 2 | 3 | 3 | 3 | 3 | | | |
| 18 | 8.0 (8.96) | 1 | | 2 | 2 | 1 | 1 | 2 | 2 | | | |
| 19 | 8.0 (8.96) | | 2 | 2 | 4 | 2 | 4 | 4 | 5 | 2 | 4 | 1 |
| | 4.0 (4.48) | | 3 | 3 | 4 | 3 | 4 | 4 | 4 | 3 | 4 | 1 |
| | 2.0 (2.24) | | 2 | 2 | 4 | 3 | 3 | 3 | 4 | 3 | 4 | 1 |
| | 1.0 (1.12) | | 2 | 2 | 3 | 2 | 4 | 4 | 4 | 2 | 4 | 1 |
| | 1.0 (1.12) | | 3 | 3 | 3 | 2 | 3 | 3 | 3 | 2 | 2 | 2 |
| | 0.5 (0.56) | | 2 | 2 | 2 | 2 | 3 | 2 | 3 | 1 | 2 | 1 |
| | 0.25 (0.28) | | 1 | 2 | 2 | 2 | 1 | 1 | 1 | 1 | 2 | 1 |
| 23 | 8.0 (8.96) | | 4 | 4 | 5 | 4 | 5 | 4 | 5 | 3 | 5 | 2 |
| 31 | 8.0 (8.96) | | 5 | 4 | 5 | 5 | 5 | 5 | 5 | 4 | 5 | 3 |
| | 4.0 (4.48) | | 4 | 5 | 5 | 4 | 4 | 4 | 5 | 1 | 4 | 3 |
| | 2.0 (2.24) | | 4 | 3 | 4 | 4 | 2 | 4 | 4 | 1 | 4 | 2 |
| | 1.0 (1.12) | | 2 | 2 | 2 | 2 | 1 | 3 | 2 | 1 | 4 | 1 |

Compounds identified as Examples 1 and 17 in this specification were tested in various field studies in an effort to further evaluate the compounds' herbicidal activity and crop tolerance.

EXPERIMENT 4

The compound 1-[5-(1,1-dimethylethyl)-3-isoxazolyl]-3-methyl-2-pyrrolidinone (Example 1) was formulated as a 50% wettable powder which contained the following percentages and ingredients by weight:

0–10, with 0 being no injury and 10 being plant death, and this number was multiplied by 10 to obtain a percent inhibition. Three replications were performed at each rate and the average percent inhibition entered in the table. Observations were made at 3 and 5 weeks after planting (and treatment). The results of this field test are reported below in Table IV (surface applied) and Table V (pre-plant incorporated).

TABLE IV

Surface Applied

| Application Rate lbs/acre (kg/ha) | Weeks After Planting | Crops | | | | Weeds | | | | | | |
|---|---|---|---|---|---|---|---|---|---|---|---|---|
| | | Soybean | Cotton | Sorghum | Corn | Pigweed | Venice Mallow | Foxtail Millet | Cocklebur | Velvetleaf | Morningglory | Foxtail Millet |
| 1.5 (1.68) | 3 | | | 13.3 | 10.0 | | | | | 100.0 | 75.0 | 98.0 |
| | 5 | | | 0 | 3.3 | | | | | 100.0 | 46.7 | 83.3 |
| 1.0 (1.12) | 3 | 43.3 | 86.7 | 0 | 0 | 99.3 | | 96.7 | 80.0 | 99.7 | 46.7 | 96.3 |
| | 5 | 86.7 | 30.0 | 0 | 3.3 | 100.0 | 100.0 | 97.3 | 50.0 | 100.0 | 13.3 | 93.3 |
| 0.75 (0.84) | 3 | 13.3 | 26.7 | 3.3 | 3.3 | 100.0 | | 88.3 | 20.0 | 99.3 | 56.7 | 84.3 |
| | 5 | 3.3 | 6.7 | 3.3 | 6.7 | 95.0 | 100.0 | 78.3 | 20.0 | 96.7 | 20.0 | 73.3 |
| 0.50 (0.56) | 3 | 0 | 20.0 | 0 | 0 | 98.3 | | 78.3 | 0 | 93.3 | 33.3 | 75.0 |
| | 5 | 0 | 0 | 6.7 | 6.7 | 73.3 | 100.0 | 30.0 | 50.0 | 96.7 | 0 | 46.7 |
| 0.25 (0.28) | 3 | 0 | 10.0 | | | 73.0 | | 30.0 | 0 | | | |
| | 5 | 0 | 0 | | | 46.7 | 96.7 | 0 | 0 | | | |

TABLE V

Pre-Plant Incorporated

| Application Rate lbs/acre (kg/ha) | Weeks After Planting | Crops | | | | Weeds | | | | | | |
|---|---|---|---|---|---|---|---|---|---|---|---|---|
| | | Soybean | Cotton | Sorghum | Corn | Pigweed | Venice Mallow | Foxtail Millet | Cocklebur | Velvetleaf | Morningglory | Foxtail Millet |
| 1.5 (1.68) | 3 | | | 43.3 | 70.0 | | | | | 100.0 | 93.3 | 97.3 |
| | 5 | | | 36.7 | | | | | | 100.0 | 78.3 | 81.7 |
| 1.0 (1.12) | 3 | 80.0 | 60.0 | 20.0 | 40.0 | 96.7 | | 90.0 | 80.0 | 100.0 | 90.0 | 90.0 |
| | 5 | 46.7 | 76.7 | 3.3 | | 73.3 | 100.0 | 80.0 | 40.0 | 100.0 | 43.3 | 70.0 |
| 0.75 (0.84) | 3 | 50.0 | 56.7 | 23.3 | 36.7 | 66.7 | | 63.3 | 80.0 | 100.0 | 80.0 | 88.3 |
| | 5 | 33.3 | 46.7 | 20.0 | | 33.3 | 100.0 | 55.0 | 60.0 | 96.7 | 50.0 | 66.7 |
| 0.50 (0.56) | 3 | 28.3 | 26.7 | 6.7 | 10.0 | 26.7 | | 30.0 | 30.0 | 99.3 | 60.0 | 78.3 |
| | 5 | 6.7 | 23.3 | 6.7 | | 0 | 100.0 | 0 | 0 | 90.0 | 16.7 | 40.0 |
| 0.25 (0.28) | 3 | 6.7 | 10.0 | | | 6.7 | | 3.3 | 0 | | | |
| | 5 | 0 | 0 | | | 0 | 93.3 | 0 | 0 | | | |

| | |
|---|---|
| 51.5 | Example 1 |
| 3.0 | Stepanol ME, sodium lauryl sulfate from Stepan Chemical Company |
| 3.0 | Polyfon O, emulsifier from Westvaco Corp. |
| 2.0 | Zeolex 7, a hydrated silicate from J. M. Huber Corp. |
| 40.5 | Barden Clay from J. M. Huber Corp. |
| 100.0 | |

The formulated compound diluted with water was both surface applied and pre-plant incorporated at various application rates to assorted crop and weed species. Plant injury ratings were made visually on a scale of

EXPERIMENT 5

Example 1 of the present invention was also field tested in an effort to evaluate the compound's ability as a postemergent herbicide. The compound was formulated as a 50% wettable powder as above and diluted with water at the application site to provide the various test compound concentrations. The formulation was applied approximately 2 weeks after planting when the plants had fully emerged. Observations were made about 1 and 2 weeks after treatment. The results were evaluated as above and are recorded below in Table VI as percent inhibition.

TABLE VI

Postemergence

| Application Rate lbs/acre (kg/ha) | Weeks After Treatment | Sorghum | Wheat | Corn | Annual Grasses | Velvetleaf | Jimsonweed | Venice Mallow |
|---|---|---|---|---|---|---|---|---|
| 3.0 (3.36) | 1 | 94.3 | 88.3 | 63.3 | 97.7 | | 100.0 | 100.0 |
| | 2 | 94.3 | 99.7 | 76.7 | 98.0 | 100.0 | 100.0 | 100.0 |
| 2.0 (2.24) | 1 | 73.3 | 63.3 | 38.3 | 76.7 | | 100.0 | 100.0 |
| | 2 | 65.0 | 80.0 | 43.3 | 85.0 | 100.0 | 100.0 | 100.0 |
| 1.0 (1.12) | 1 | 53.3 | 30.0 | 26.7 | 43.3 | | 100.0 | 91.7 |
| | 2 | 50.0 | 0 | 33.3 | 50.0 | 95.0 | 100.0 | 100.0 |

EXPERIMENT 6

A field study was also conducted in Great Britain to determine the efficacy and selectivity of Example 1 of the present invention against a variety of crop and weed species. The compound was formulated as a 50% wettable powder as described above. The formulated compound was then diluted with water and applied postemergence approximately 4 weeks after planting. Observations were made at various intervals thereafter to determine the compound's effect against the crop species barley and wheat by comparing crop injury to untreated control plots, as well as the compound's ability to control certain weed species. Control ratings are given in percentage of control compared to untreated control plots based upon visual inspection. These results appear in Table VII below.

TABLE VII

| Observation | Postemergence Days After Treatment | Rate kg/ha | Percent |
|---|---|---|---|
| Barley Injury | 7 | 2.0 | 0.6 |
| | | 1.0 | 0.6 |
| | | 0.5 | 0 |
| | | 0.25 | 0.6 |
| | | 0.125 | 0 |
| | | Control | 0 |
| | 13 | 2.0 | 37.5 |
| | | 1.0 | 31.5 |
| | | 0.5 | 9.4 |
| | | 0.25 | 2.8 |
| | | 0.125 | 4.7 |
| | | Control | 0 |
| | 22 | 2.0 | 96.0 |
| | | 1.0 | 96.0 |
| | | 0.5 | 84.2 |
| | | 0.25 | 31.5 |
| | | 0.125 | 9.4 |
| | | Control | 0 |
| Wheat Injury | 7 | 2.0 | 0.6 |
| | | 1.0 | 0.6 |
| | | 0.5 | 0.6 |
| | | 0.25 | 1.2 |
| | | 0.125 | 0 |
| | | Control | 0 |
| | 13 | 2.0 | 6.6 |
| | | 1.0 | 3.9 |
| | | 0.5 | 0.6 |
| | | 0.25 | 0.6 |
| | | 0.125 | 0.6 |
| | | Control | 0 |
| | 22 | 2.0 | 93.4 |
| | | 1.0 | 88.8 |
| | | 0.5 | 9.4 |
| | | 0.25 | 2.8 |
| | | 0.125 | 2.3 |
| | | Control | 0 |
| Control of Blackgrass | 13 | 2.0 | 68.5 |
| | | 1.0 | 73.5 |
| | | 0.5 | 68.5 |
| | | 0.25 | 22.3 |
| | | 0.125 | 18.8 |
| | | Control | 0 |
| | 22 | 2.0 | 98.8 |
| | | 1.0 | 100.0 |
| | | 0.5 | 94.4 |
| | | 0.25 | 84.2 |
| | | 0.125 | 26.5 |
| | | Control | 0 |
| Control of Catchweed Bedstraw | 13 | 2.0 | 94.4 |
| | | 1.0 | 84.2 |
| | | 0.5 | 44.6 |
| | | 0.25 | 44.6 |
| | | 0.125 | 9.4 |
| | | Control | 0 |
| | 22 | 2.0 | 100.0 |
| | | 1.0 | 97.6 |
| | | 0.5 | 62.5 |
| | | 0.25 | 62.5 |
| | | 0.125 | 6.6 |
| | | Control | 0 |
| Control of Wild Chamomile | 13 | 2.0 | 11.1 |
| | | 1.0 | 11.1 |
| | | 0.5 | 3.3 |
| | | 0.25 | 3.3 |
| | | 0.125 | 3.3 |
| | | Control | 0 |
| | 22 | 2.0 | 100.0 |
| | | 1.0 | 98.8 |
| | | 0.5 | 97.2 |
| | | 0.25 | 90.6 |
| | | 0.125 | 18.8 |
| | | Control | 0 |
| Control of Annual Bluegrass | 13 | 2.0 | 55.4 |
| | | 1.0 | 86.7 |
| | | 0.5 | 62.5 |
| | | 0.25 | 55.4 |
| | | 0.125 | 50.0 |
| | | Control | 0 |
| | 22 | 2.0 | 99.4 |
| | | 1.0 | 99.4 |
| | | 0.5 | 88.8 |
| | | 0.25 | 81.3 |
| | | 0.125 | 68.5 |
| | | Control | 0 |
| Control of Ladysthumb | 13 | 2.0 | 100.0 |
| | | 1.0 | 98.8 |
| | | 0.5 | 99.4 |
| | | 0.25 | 93.4 |
| | | 0.125 | 55.4 |
| | | Control | 0 |
| | 22 | 2.0 | 100.0 |
| | | 1.0 | 100.0 |
| | | 0.5 | 100.0 |
| | | 0.25 | 97.6 |
| | | 0.125 | 93.4 |
| | | Control | 0 |
| Control of Common Chickweed | 13 | 2.0 | 44.6 |
| | | 1.0 | 37.5 |
| | | 0.5 | 5.6 |
| | | 0.25 | 3.3 |
| | | 0.125 | 3.3 |
| | | Control | 0 |
| | 22 | 2.0 | 98.8 |
| | | 1.0 | 95.3 |
| | | 0.5 | 50.0 |
| | | 0.25 | 73.5 |
| | | 0.125 | 9.4 |
| | | Control | 0 |
| Control of Ivyleaf Speedwell | 13 | 2.0 | 44.6 |
| | | 1.0 | 15.8 |
| | | 0.5 | 1.8 |
| | | 0.25 | 3.9 |
| | | 0.125 | 2.3 |
| | | Control | 0 |
| | 22 | 2.0 | 97.6 |
| | | 1.0 | 77.7 |
| | | 0.5 | 9.4 |
| | | 0.25 | 22.3 |
| | | 0.125 | 4.7 |
| | | Control | 0 |
| Control of Wild Violet | 13 | 2.0 | 73.5 |
| | | 1.0 | 90.6 |
| | | 0.5 | 68.5 |
| | | 0.25 | 37.5 |
| | | 0.125 | 44.6 |
| | | Control | 0 |
| | 22 | 2.0 | 100.0 |
| | | 1.0 | 100.0 |
| | | 0.5 | 96.7 |
| | | 0.25 | 84.2 |
| | | 0.125 | 84.2 |
| | | Control | 0 |

EXPERIMENT 7

The intermediate identified as Example 17 in the present invention, 4-chloro-N-[5-(1,1-dimethylethyl)-3-isoxazolyl]-2-methylbutanamide, was also field tested to further evaluate the compound's herbicidal efficacy.

The compound was formulated as a 50% wettable powder which contained the following ingredients and percentages by weight:

| | |
|---|---|
| 51.5 | Example 17 |
| 5.0 | Stepanol ME, sodium lauryl sulfate from Stepan Chemical Company |
| 5.0 | Polyfon O, emulsifier from Westvaco Corp. |
| 5.0 | Zeolex 7, a hydrated silicate from J. M. Huber Corp. |
| 33.5 | Barden Clay from J. M. Huber Corp. |
| 100.0 | |

The formulated compound was diluted with water and both surface applied and pre-plant incorporated to the soil surface prior to planting various crop and weed species. Observations were made 3 and 6 weeks after planting and the results are recorded as percent inhibition in Table VIII (surface applied) and Table IX (pre-plant incorporated) below.

TABLE VIII

Surface Applied

| Application Rate lbs/acre (kg/ha) | | Weeks After Planting | Crops | | | | | | |
|---|---|---|---|---|---|---|---|---|---|
| | | | Barley | Wheat | Rice | Cotton | Soybean | Sorghum | Corn |
| 4.0 | (4.48) | 3 | | | 0 | 70.0 | 46.7 | 10.0 | 0 |
| | | 6 | | | 0 | 53.3 | 18.3 | 0 | 0 |
| 2.0 | (2.24) | 3 | 16.7 | 0 | 0 | 26.7 | 23.3 | 3.3 | 0 |
| | | 6 | 5.0 | 0 | 1.7 | 13.3 | 3.3 | 0 | 0 |
| 1.0 | (1.12) | 3 | 16.7 | 3.3 | 0 | 0 | 0 | 0 | 0 |
| | | 6 | 0 | 0 | 0 | 3.3 | 0 | 0 | 0 |
| 0.5 | (0.56) | 3 | 10.0 | 3.3 | 0 | 6.7 | 6.7 | 0 | 0 |
| | | 6 | 0 | 0 | 0 | 0 | 0 | 0 | 6.7 |
| 0.25 | (0.28) | 3 | 6.7 | 3.3 | | | | | |
| | | 6 | 0 | 0 | | | | | |

| Application Rate lbs/acre (kg/ha) | | Weeks After Planting | Weeds | | | | | | | | |
|---|---|---|---|---|---|---|---|---|---|---|---|
| | | | Annual Grasses | Velvetleaf | Morningglory | Foxtail Millet | Redroot Pigwood | Wild Oats | Indian Mustard | Green Foxtail | Barnyardgrass |
| 4.0 | (4.48) | 3 | — | | 71.7 | 53.8 | | | | | 16.7 |
| | | 6 | 0 | 87.5 | 30.0 | 30 | 70 | | | | 15.0 |
| 2.0 | (2.24) | 3 | | | 50.0 | 38.4 | 98.3 | 13.3 | 94.3 | 60 | 0 |
| | | 6 | 0 | 82.5 | 22.5 | 25.9 | 69.2 | 0 | 88.3 | 53.3 | 15.0 |
| 1.0 | (1.12) | 3 | | | 23.4 | 8.4 | 86.7 | 16.7 | 81.7 | 66.7 | 0 |
| | | 6 | 0 | 52.5 | 13.3 | 3.4 | 64.2 | 0 | 46.7 | 0 | 10 |
| 0.5 | (0.56) | 3 | | | 11.7 | 12.5 | 30.0 | 10.0 | 46.7 | 16.7 | 0 |
| | | 6 | 6.7 | 23.4 | 8.4 | 5.9 | 32.1 | 0 | 40.0 | 0 | 0 |
| 0.25 | (0.28) | 3 | | | | | 10 | 3.3 | 36.7 | 13.3 | |
| | | 6 | | | | | 0 | 0 | 13.3 | 0 | |

TABLE IX

Pre-Plant Incorporated

| Application Rate lbs/acre (kg/ha) | | Weeks After Planting | Crops | | | | | | |
|---|---|---|---|---|---|---|---|---|---|
| | | | Barley | Wheat | Rice | Cotton | Soybean | Sorghum | Corn |
| 4.0 | (4.48) | 3 | | | 0 | 6.7 | 40.0 | 0 | 0 |
| | | 6 | | | 0 | 0 | 10.0 | 0 | 0 |
| 2.0 | (2.24) | 3 | 11.7 | 6.7 | 6.7 | 10.0 | 28.3 | 0 | 0 |
| | | 6 | 0 | 0 | 6.7 | 6.7 | 5.0 | 6.7 | 0 |
| 1.0 | (1.12) | 3 | 6.7 | 3.3 | 0 | 20.0 | 0 | 0 | 0 |
| | | 6 | 0 | 0 | 0 | 10.0 | 0 | 5.0 | 0 |
| 0.5 | (0.56) | 3 | 0 | 0 | 0 | 16.7 | 3.3 | 0 | 0 |
| | | 6 | 0 | 0 | 3.3 | 10.0 | 0 | 0 | 0 |
| 0.25 | (0.28) | 3 | 0 | 0 | | | | | |
| | | 6 | 0 | 0 | | | | | |

| Application Rate lbs/acre (kg/ha) | | Weeks After Planting | Weeds | | | | | | | |
|---|---|---|---|---|---|---|---|---|---|---|
| | | | Redroot Pigweed | Wild Oat | Wild Mustard | Green Foxtail | Barnyardgrass | Foxtail Millet | Velvetleaf | Morningglory |
| 4.0 | (4.48) | 3 | 16.7 | | | | 0 | 5.6 | | 18.3 |
| | | 6 | 72.5 | | | | 10 | 3.4 | 10.4 | 10.0 |
| 2.0 | (2.24) | 3 | 38.4 | 11.7 | 30 | 23.3 | 23 | 6.7 | | 5.0 |
| | | 6 | 32.2 | 0 | 16.7 | 0 | 10 | 10 | 0 | 0 |
| 1.0 | (1.12) | 3 | 21.7 | 6.7 | 30 | 23.3 | 0 | 10 | | 6.7 |
| | | 6 | 6.7 | 0 | 26.7 | 0 | 0 | 6.7 | 0 | 0 |
| 0.5 | (0.56) | 3 | 16.7 | 6.7 | 0 | 0 | 0 | 2.2 | | 5 |

TABLE IX-continued

| | | | Pre-Plant Incorporated | | | | | | |
|---|---|---|---|---|---|---|---|---|---|
| | | 6 | 4.4 | 0 | 0 | 0 | 8.3 | 8.4 | 0 | 0 |
| 0.25 | (0.28) | 3 | 0 | 6.7 | 0 | 0 | | | | |
| | | 6 | 20.0 | 0 | 0 | 0 | | | | |

EXPERIMENT 8

Example 17 of the present invention was also evaluated in a postemergence field study. The compound was formulated as a 50% wettable powder as outlined above. The emerged plants were treated about 2 weeks after planting and observations were made 1 and 2 weeks after treatment. Table X below presents the results of this field test as percent inhibition.

TABLE X

| | | Postemergence | | | | | | |
|---|---|---|---|---|---|---|---|---|
| Application Rate lbs/acre (kg/ha) | Weeks After Treatment | Rice | Wheat | Pigweed | Wild Oat | Indian Mustard | Barnyard-grass | Giant Foxtail |
| 1.0 | 1 | 0 | 6.7 | 86.7 | 0 | 56.7 | 0 | 0 |
| | 2 | 0 | 6.7 | 85.0 | 0 | 100.0 | 0 | 0 |
| 0.5 | 1 | 0 | 10.0 | 46.7 | 0 | 16.7 | 0 | 0 |
| | 2 | 0 | 0 | 16.7 | 0 | 96.7 | 0 | 0 |
| 0.25 | 1 | 0 | 6.7 | 6.7 | 0 | 10.0 | 0 | 0 |
| | 2 | 0 | 0 | 10.0 | 0 | 33.3 | 0 | 0 |
| 0.125 | 1 | 0 | 0 | 3.3 | 0 | 3.3 | 0 | 0 |
| | 2 | 0 | 0 | 0 | 0 | 0 | 0 | 0 |

As noted above, the compounds and intermediates of the present invention may also be used in combination with one or more herbicides. Such combinations are preferred when a broader spectrum of weed control is desired than either herbicide can provide when used alone. For example, the present compounds may be combined with one or more grass herbicides. Preferred grass herbicides to be employed in these combinations include the dinitroanilines, such as trifluralin, benefin, butralin, chlornidine, dinitramine, ethalfluralin, fluchloralin, isopropalin, nitralin, oryzalin, pendimethalin, prodiamine, profluralin, prosulfalin, and the like. The most preferred combination of the present invention is comprised of trifluralin and 1-[5-(1,1-dimethylethyl)-3-isoxazolyl]-3-methyl-2-pyrrolidinone. Other herbicides which may be used in combination with a presently disclosed active ingredient include alachlor, ametryn, amitrole, atrazine, bentazon, bifenox, butachlor, butam, buthidazole, butylate, chloramben, chlorbromuron, cyanazine, dichlorprop, diuron, dinoseb, EPTC, fenac, fluometuron, linuron, methazole, metolachlor, metribuzin, nitrofen, norflurazon, pebulate, perfluidone, prometon, prometryn, propachlor, simazine, tebuthiuron, terbutryn, triallate, triclopyr, propanil, vernolate and the like.

Also provided by this invention is a method for controlling undesired plants which comprises applying to the plants a growth inhibiting amount of a combination of a present compound or intermediate together with one or more herbicides. The application rate desired for each of the individual herbicides in the combination is dependent on a number of factors, including the type of weeds and grasses to be controlled, the herbicides that will be used in the combination, climate and soil conditions, the weed population and related factors. Generally, the present compounds or intermediates will be employed in combination with other herbicides in a ratio of about one to about ten parts by weight of a present active agent and about ten to about one part by weight of another herbicide. More preferable ratios of active ingredients will be from about one to about five parts by weight of a present compound or intermediate and about five to about one part by weight of another herbicide. A particularly preferred combination will contain the component herbicides in a weight ratio of about one to one. The combinations will be applied at rates which are effective to control the undesired plants to the desired degree.

The combinations provided herein are formulated in the identical manner which was described for the present novel compounds and intermediates alone, and at similar concentrations. The active components of the combination may be combined as technical materials and later formulated as a whole, or formulated individually and applied either as a combination or individually to the locus of the undesired plants.

The following is an example of a typical herbicidal composition containing a combination of the invention.

| Tank-Mix Composition | |
|---|---|
| Ingredient | Concentration by Weight (Percent) |
| 1-[5-(1,1-Dimethylethyl)-3-isoxazolyl]-2-piperidinone formulated as a 50% wettable powder | 60.0 |
| Trifluralin formulated as a 4EC | 40.0 |
| | 100.0 |

The wettable powder formulation containing 50% by weight of the active ingredient is added to water and the mixture agitated while adding the emulsifiable concentrate containing the trifluralin at the rate of 4 lbs/gal (0.48 kg/l.). The mixture is sprayed on the soil surface and then typically incorporated at a depth of about 3 to 4 inches prior to planting.

The herbicidal activity of representative combinations of the present invention is illustrated by the following field studies.

EXPERIMENT 9

A field study was conducted in Mississippi using Example 1 of the invention both alone and in combination with trifluralin on cotton against a wide variety of weed species. Trifluralin was formulated as an emulsifiable concentrate at a test compound concentration of 4 lbs/gallon (0.48 kg/l.) and pre-plant incorporated into the soil. Example 1, formulated as a 50% wettable powder as detailed above, was then surface applied as an overlay treatment following the trifluralin incorporation. The results of this test appear below in Table XI.

TABLE XI

| Observation | Days After Treatment | Treatment | Rate kg/ha | Percent |
|---|---|---|---|---|
| Cotton Emergence | 12 | Example 1 + Trifluralin | 0.84 + 1.68 | 100.0 |
| | | | 0.56 + 0.84 | 100.0 |
| | | | 0.43 + 0.84 | 100.0 |
| | | | 0.28 + 0.84 | 100.0 |
| | | | 0.14 + 0.84 | 100.0 |
| | | Example 1 | 0.84 | 100.0 |
| | | | 0.56 | 100.0 |
| | | | 0.43 | 100.0 |
| | | | 0.28 | 100.0 |
| | | | 0.14 | 100.0 |
| | | Untreated Control | | 100.0 |
| Cotton Injury | 29 | Example 1 + Trifluralin | 0.84 + 1.68 | 100.0 |
| | | | 0.56 + 0.84 | 89.3 |
| | | | 0.43 + 0.84 | 68.3 |
| | | | 0.28 + 0.84 | 33.3 |
| | | | 0.14 + 0.84 | 15.0 |
| | | Example 1 | 0.84 | 100.0 |
| | | | 0.56 | 100.0 |
| | | | 0.43 | 92.7 |
| | | | 0.28 | 56.7 |
| | | | 0.14 | 13.3 |
| | | Untreated Control | | 0 |
| | 74 | Example 1 + Trifluralin | 0.84 + 1.68 | 100.0 |
| | | | 0.56 + 0.84 | 98.0 |
| | | | 0.43 + 0.84 | 73.3 |
| | | | 0.28 + 0.84 | 36.7 |
| | | | 0.14 + 0.84 | 8.3 |
| | | Example 1 | 0.84 | 100.0 |
| | | | 0.56 | 100.0 |
| | | | 0.43 | 96.7 |
| | | | 0.28 | 58.3 |
| | | | 0.14 | 15.0 |
| | | Untreated Control | | 0 |
| Control of Redroot Pigweed | 29 | Example 1 + Trifluralin | 0.84 + 1.68 | 100.0 |
| | | | 0.56 + 0.84 | 100.0 |
| | | | 0.43 + 0.84 | 100.0 |
| | | | 0.28 + 0.84 | 99.7 |
| | | | 0.14 + 0.84 | 100.0 |
| | | Example 1 | 0.84 | 100.0 |
| | | | 0.56 | 98.3 |
| | | | 0.43 | 91.7 |
| | | | 0.28 | 73.3 |
| | | | 0.14 | 66.7 |
| | | Untreated Control | | 0 |
| | 74 | Example 1 + Trifluralin | 0.84 + 1.68 | 99.7 |
| | | | 0.56 + 0.84 | 96.3 |
| | | | 0.43 + 0.84 | 98.3 |
| | | | 0.28 + 0.84 | 96.7 |
| | | | 0.14 + 0.84 | 97.7 |
| | | Example 1 | 0.84 | 85.0 |
| | | | 0.56 | 56.7 |
| | | | 0.43 | 26.7 |
| | | | 0.28 | 6.7 |
| | | | 0.14 | 6.7 |
| | | Untreated Control | | 0 |
| Control of Large Crabgrass | 74 | Example 1 + Trifluralin | 0.84 + 1.68 | 100.0 |
| | | | 0.56 + 0.84 | 100.0 |
| | | | 0.43 + 0.84 | 100.0 |
| | | | 0.28 + 0.84 | 100.0 |
| | | | 0.14 + 0.84 | 100.0 |
| | | Example 1 | 0.84 | 83.3 |
| | | | 0.56 | 26.7 |
| | | | 0.43 | 16.7 |
| | | | 0.28 | 0 |
| | | | 0.14 | 0 |
| | | Untreated Control | | 0 |
| Control of Goosegrass | 74 | Example 1 + Trifluralin | 0.84 + 1.68 | 100.0 |
| | | | 0.56 + 0.84 | 100.0 |
| | | | 0.43 + 0.84 | 100.0 |
| | | | 0.28 + 0.84 | 100.0 |
| | | | 0.14 + 0.84 | 100.0 |
| | | Example 1 | 0.84 | 85.0 |
| | | | 0.56 | 33.3 |
| | | | 0.43 | 16.7 |
| | | | 0.28 | 0 |
| | | | 0.14 | 0 |
| | | Untreated Control | | 0 |
| Control of Common Purslane | 29 | Example 1 + Trifluralin | 0.84 + 1.68 | 100.0 |
| | | | 0.56 + 0.84 | 100.0 |
| | | | 0.43 + 0.84 | 100.0 |
| | | | 0.28 + 0.84 | 100.0 |
| | | | 0.14 + 0.84 | 100.0 |
| | | Example 1 | 0.84 | 100.0 |
| | | | 0.56 | 100.0 |
| | | | 0.43 | 96.0 |
| | | | 0.28 | 73.3 |
| | | | 0.14 | 73.3 |
| | | Untreated Control | | 0 |
| Control of Foxtail Millet | 29 | Example 1 + Trifluralin | 0.84 + 1.68 | 100.0 |
| | | | 0.56 + 0.84 | 100.0 |
| | | | 0.43 + 0.84 | 100.0 |
| | | | 0.28 + 0.84 | 100.0 |
| | | | 0.14 + 0.84 | 100.0 |
| | | Example 1 | 0.84 | 100.0 |
| | | | 0.56 | 99.3 |
| | | | 0.43 | 97.3 |
| | | | 0.28 | 91.7 |
| | | | 0.14 | 66.7 |
| | | Untreated Control | | 0 |
| | 74 | Example 1 + Trifluralin | 0.84 + 1.68 | 100.0 |
| | | | 0.56 + 0.84 | 100.0 |
| | | | 0.43 + 0.84 | 100.0 |
| | | | 0.28 + 0.84 | 100.0 |
| | | | 0.14 + 0.84 | 100.0 |
| | | Example 1 | 0.84 | 100.0 |
| | | | 0.56 | 100.0 |
| | | | 0.43 | 100.0 |
| | | | 0.28 | 93.3 |
| | | | 0.14 | 76.7 |
| | | Untreated Control | | 0 |
| Control of Prickly Sida | 29 | Example 1 + Trifluralin | 0.84 + 1.68 | 98.3 |
| | | | 0.56 + 0.84 | 96.0 |
| | | | 0.43 + 0.84 | 96.3 |
| | | | 0.28 + 0.84 | 96.0 |
| | | | 0.14 + 0.84 | 86.7 |
| | | Example 1 | 0.84 | 97.3 |
| | | | 0.56 | 97.7 |
| | | | 0.43 | 96.0 |
| | | | 0.28 | 93.3 |
| | | | 0.14 | 86.7 |
| | | Untreated Control | | 0 |
| | 74 | Example 1 + Trifluralin | 0.84 + 1.68 | 100.0 |
| | | | 0.56 + 0.84 | 100.0 |
| | | | 0.43 + 0.84 | 100.0 |
| | | | 0.28 + 0.84 | 100.0 |
| | | | 0.14 + 0.84 | 86.7 |
| | | Example 1 | 0.84 | 100.0 |
| | | | 0.56 | 100.0 |
| | | | 0.43 | 100.0 |
| | | | 0.28 | 100.0 |
| | | | 0.14 | 93.3 |
| | | Untreated Control | | 0 |

EXPERIMENT 10

A field study was also conducted in North Carolina using Example 1 both alone and in combination with other herbicides on peanuts against a variety of weeds. Example 1 was formulated as a 50% wettable powder as has been described previously. This formulation was also tank-mixed with each of three other herbicides as follows: ethalfluralin as an emulsifiable concentrate at 3 lbs/gallon (0.36 kg/l.); alachlor as an emulsifiable concentrate at 4 lbs/gallon (0.48 kg/l.); and metolachlor as an emulsifiable concentrate at 8 lbs/gallon (0.96 kg/l.). The various formulations were surface applied onto the soil following planting the same day. Observations were then recorded following visual comparison of treated plots and untreated controls. These results appear below in Table XII.

TABLE XII

| Observation | Days After Treatment | Surface Applied Treatment | Rate kg/ha | Percent |
|---|---|---|---|---|
| Peanut Injury | 28 | Example 1 + Ethalfluralin | 0.56 + 2.52 | 53.3 |
| | | | 0.28 + 1.25 | 15.0 |
| | | Example 1 + Alachlor | 0.28 + 2.24 | 16.7 |
| | | Example 1 + Metolachlor | 0.28 + 2.24 | 16.7 |
| | | Example 1 | 0.84 | 81.7 |
| | | | 0.56 | 56.7 |
| | | | 0.43 | 36.7 |
| | | | 0.28 | 16.7 |
| | | | 0.14 | 8.3 |
| | | Untreated Control | | 0 |
| | 97 | Example 1 + Ethalfluralin | 0.56 + 2.52 | 40.0 |
| | | | 0.28 + 1.25 | 6.7 |
| | | Example 1 + Alachlor | 0.28 + 2.24 | 3.3 |
| | | Example 1 + Metolachlor | 0.28 + 2.24 | 0 |
| | | Example 1 | 0.84 | 85.0 |
| | | | 0.56 | 56.7 |
| | | | 0.43 | 0 |
| | | | 0.28 | 0 |
| | | | 0.14 | 0 |
| | | Untreated Control | | 0 |
| Control of Lambsquarters | 28 | Example 1 + Ethalfluralin | 0.56 + 2.52 | 99.3 |
| | | | 0.28 + 1.25 | 98.3 |
| | | Example 1 + Alachlor | 0.28 + 2.24 | 98.0 |
| | | Example 1 + Metolachlor | 0.28 + 2.24 | 98.0 |
| | | Example 1 | 0.84 | 99.0 |
| | | | 0.56 | 99.0 |
| | | | 0.43 | 98.3 |
| | | | 0.28 | 95.0 |
| | | | 0.14 | 75.0 |
| | | Untreated Control | | 0 |
| | 97 | Example 1 + Ethalfluralin | 0.56 + 2.52 | 100.0 |
| | | | 0.28 + 1.25 | 100.0 |
| | | Example 1 + Alachlor | 0.28 + 2.24 | 100.0 |
| | | Example 1 + Metolachlor | 0.28 + 2.24 | 98.7 |
| | | Example 1 | 0.84 | 100.0 |
| | | | 0.56 | 98.3 |
| | | | 0.43 | 93.3 |
| | | | 0.28 | 100.0 |
| | | | 0.14 | 98.7 |
| | | Untreated Control | | 0 |
| Control of Jimsonweed | 28 | Example 1 + Ethalfluralin | 0.56 + 2.52 | 99.0 |
| | | | 0.28 + 1.25 | 96.0 |
| | | Example 1 + Alachlor | 0.28 + 2.24 | 82.3 |
| | | Example 1 + Metolachlor | 0.28 + 2.24 | 81.7 |
| | | Example 1 | 0.84 | 99.0 |
| | | | 0.56 | 97.3 |
| | | | 0.43 | 90.0 |
| | | | 0.28 | 66.7 |
| | | | 0.14 | 43.3 |
| | | Untreated Control | | 0 |
| Control of Large Crabgrass | 28 | Example 1 + Ethalfluralin | 0.56 + 2.52 | 98.7 |
| | | | 0.28 + 1.25 | 97.0 |
| | | Example 1 + Alachlor | 0.28 + 2.24 | 98.3 |
| | | Example 1 + Metolachlor | 0.28 + 2.24 | 98.3 |
| | | Example 1 | 0.84 | 92.3 |
| | | | 0.56 | 85.0 |
| | | | 0.43 | 70.0 |
| | | | 0.28 | 38.3 |
| | | | 0.14 | 23.3 |
| | | Untreated Control | | 0 |
| | 97 | Example 1 + | 0.56 + 2.52 | 92.3 |

TABLE XII-continued

| Observation | Days After Treatment | Treatment | Rate kg/ha | Percent |
|---|---|---|---|---|
| | | Surface Applied | | |
| | | Ethalfluralin | 0.28 + 1.25 | 90.7 |
| | | Example 1 + Alachlor | 0.28 + 2.24 | 96.0 |
| | | Example 1 + Metolachlor | 0.28 + 2.24 | 97.7 |
| | | Example 1 | 0.84 | 63.3 |
| | | | 0.56 | 50.0 |
| | | | 0.43 | 30.0 |
| | | | 0.28 | 0 |
| | | | 0.14 | 0 |
| | | Untreated Control | | 0 |
| Control of Ivyleaf Morningglory | 28 | Example 1 + Ethalfluralin | 0.56 + 2.52 0.28 + 1.25 | 80.0 53.3 |
| | | Example 1 + Alachlor | 0.28 + 2.24 | 71.7 |
| | | Example 1 + Metolachlor | 0.28 + 2.24 | 66.7 |
| | | Example 1 | 0.84 | 88.3 |
| | | | 0.56 | 86.7 |
| | | | 0.43 | 53.3 |
| | | | 0.28 | 33.3 |
| | | | 0.14 | 33.3 |
| | | Untreated Control | | 0 |
| | 97 | Example 1 + Ethalfluralin | 0.56 + 2.52 0.28 + 1.25 | 50.0 63.3 |
| | | Example 1 + Alachlor | 0.28 + 2.24 | 76.7 |
| | | Example 1 + Metolachlor | 0.28 + 2.24 | 65.0 |
| | | Example 1 | 0.84 | 60.0 |
| | | | 0.56 | 63.3 |
| | | | 0.43 | 56.7 |
| | | | 0.28 | 66.7 |
| | | | 0.14 | 53.3 |
| | | Untreated Control | | 0 |
| Control of Prickly Sida | 28 | Example 1 + Ethalfluralin | 0.56 + 2.52 0.28 + 1.25 | 98.7 97.0 |
| | | Example 1 + Alachlor | 0.28 + 2.24 | 97.3 |
| | | Example 1 + Metolachlor | 0.28 + 2.24 | 97.3 |
| | | Example 1 | 0.84 | 98.0 |
| | | | 0.56 | 97.0 |
| | | | 0.43 | 96.0 |
| | | | 0.28 | 83.3 |
| | | | 0.14 | 86.7 |
| | | Untreated Control | | 0 |
| | 97 | Example 1 + Ethalfluralin | 0.56 + 2.52 0.28 + 1.25 | 95.3 96.3 |
| | | Example 1 + Alachlor | 0.28 + 2.24 | 96.7 |
| | | Example 1 + Metolachlor | 0.28 + 2.24 | 97.7 |
| | | Example 1 | 0.84 | 97.0 |
| | | | 0.56 | 95.7 |
| | | | 0.43 | 95.0 |
| | | | 0.28 | 95.0 |
| | | | 0.14 | 86.7 |
| | | Untreated Control | | 0 |

EXPERIMENT 11

A field study was conducted in Florida to evaluate the herbicidal activity and crop tolerance of Example 1 of the present invention both alone and in combination with ethalfluralin and linuron. Example 1 was formulated as a 50% wettable powder as above. When used in combination, Example 1 was tank mixed with ethalfluralin formulated as an aqueous suspension at a concentration of 4 lbs/gallon (0.48 kg/l.) and linuron formulated as a 50% wettable powder. The formulations were applied over the top to emerged weeds for pre-emergence weed control in no-till soybeans. Evaluations were made as above and the results appear below in Table XIII.

TABLE XIII

| Observation | Days After Treatment | Treatment | Rate kg/ha | Percent |
|---|---|---|---|---|
| Soybean Injury | 7 | Example 1 + Ethalfluralin + Linuron | 0.84 + 0.84 + 0.56 | 10.0 |
| | | | 0.56 + 0.84 + 0.56 | 6.7 |
| | | | 0.43 + 0.84 + 0.56 | 6.7 |
| | | | 0.28 + 0.84 + 0.56 | 3.3 |

TABLE XIII-continued

| Observation | Days After Treatment | Treatment | Rate kg/ha | Percent |
|---|---|---|---|---|
| | | Example 1 | 0.84 | 3.3 |
| | | | 0.56 | 3.3 |
| | | | 0.43 | 6.7 |
| | | | 0.28 | 3.3 |
| | | Untreated Control | | 0 |
| | 26 | Example 1 | 0.84 + 0.84 + 0.56 | 36.7 |
| | | + Ethalfluralin | 0.56 + 0.84 + 0.56 | 0 |
| | | + Linuron | 0.43 + 0.84 + 0.56 | 0 |
| | | | 0.28 + 0.84 + 0.56 | 3.3 |
| | | Example 1 | 0.84 | 16.7 |
| | | | 0.56 | 3.3 |
| | | | 0.43 | 0 |
| | | | 0.28 | 0 |
| | | Untreated Control | | 0 |
| Control of Velvetleaf | 7 | Example 1 | 0.84 + 0.84 + 0.56 | 100.0 |
| | | + Ethalfluralin | 0.56 + 0.84 + 0.56 | 100.0 |
| | | + Linuron | 0.43 + 0.84 + 0.56 | 100.0 |
| | | | 0.28 + 0.84 + 0.56 | 100.0 |
| | | Example 1 | 0.84 | 100.0 |
| | | | 0.56 | 100.0 |
| | | | 0.43 | 100.0 |
| | | | 0.28 | 0.0 |
| | | Untreated Control | | 0 |
| | 26 | Example 1 | 0.84 + 0.84 + 0.56 | 100.0 |
| | | + Ethalfluralin | 0.56 + 0.84 + 0.56 | 100.0 |
| | | + Linuron | 0.43 + 0.84 + 0.56 | 100.0 |
| | | | 0.28 + 0.84 + 0.56 | 100.0 |
| | | Example 1 | 0.84 | 99.3 |
| | | | 0.56 | 98.0 |
| | | | 0.43 | 95.7 |
| | | | 0.28 | 48.7 |
| | | Untreated Control | | 0 |
| Control of Redroot Pigweed | 7 | Example 1 | 0.84 + 0.84 + 0.56 | 100.0 |
| | | + Ethalfluralin | 0.56 + 0.84 + 0.56 | 100.0 |
| | | + Linuron | 0.43 + 0.84 + 0.56 | 99.7 |
| | | | 0.28 + 0.84 + 0.56 | 98.3 |
| | | Example 1 | 0.84 | 98.7 |
| | | | 0.56 | 77.7 |
| | | | 0.43 | 86.7 |
| | | | 0.28 | 13.3 |
| | | Untreated Control | | 0 |
| | 26 | Example 1 | 0.84 + 0.84 + 0.56 | 100.0 |
| | | + Ethalfluralin | 0.56 + 0.84 + 0.56 | 100.0 |
| | | + Linuron | 0.43 + 0.84 + 0.56 | 100.0 |
| | | | 0.28 + 0.84 + 0.56 | 100.0 |
| | | Example 1 | 0.84 | 100.0 |
| | | | 0.56 | 86.7 |
| | | | 0.43 | 70.0 |
| | | | 0.28 | 26.7 |
| | | Untreated Control | | 0 |
| Control of Spurred Anoda | 7 | Example 1 | 0.84 + 0.84 + 0.56 | 100.0 |
| | | + Ethalfluralin | 0.56 + 0.84 + 0.56 | 100.0 |
| | | + Linuron | 0.43 + 0.84 + 0.56 | 100.0 |
| | | | 0.28 + 0.84 + 0.56 | 100.0 |
| | | Example 1 | 0.84 | 100.0 |
| | | | 0.56 | 100.0 |
| | | | 0.43 | 100.0 |
| | | | 0.28 | 0.0 |
| | | Untreated Control | | 0 |
| | 26 | Example 1 | 0.84 + 0.84 + 0.56 | 100.0 |
| | | + Ethalfluralin | 0.56 + 0.84 + 0.56 | 100.0 |
| | | + Linuron | 0.43 + 0.84 + 0.56 | 100.0 |
| | | | 0.28 + 0.84 + 0.56 | 100.0 |
| | | Example 1 | 0.84 | 100.0 |
| | | | 0.56 | 98.7 |
| | | | 0.43 | 97.7 |
| | | | 0.28 | 49.3 |
| | | Untreated Control | | 0 |
| Control of Sicklepod | 7 | Example 1 | 0.84 + 0.84 + 0.56 | 100.0 |
| | | + Ethalfluralin | 0.56 + 0.84 + 0.56 | 100.0 |
| | | + Linuron | 0.43 + 0.84 + 0.56 | 99.7 |
| | | | 0.28 + 0.84 + 0.56 | 100.0 |
| | | Example 1 | 0.84 | 98.3 |
| | | | 0.56 | 78.3 |
| | | | 0.43 | 80.0 |
| | | | 0.28 | 20.0 |
| | | Untreated Control | | 0 |
| | 26 | Example 1 | 0.84 + 0.84 + 0.56 | 100.0 |
| | | + Ethalfluralin | 0.56 + 0.84 + 0.56 | 100.0 |
| | | + Linuron | 0.43 + 0.84 + 0.56 | 100.0 |

TABLE XIII-continued

| Observation | Days After Treatment | Treatment | Rate kg/ha | Percent |
|---|---|---|---|---|
| | | | 0.28 + 0.84 + 0.56 | 100.0 |
| | | Example 1 | 0.84 | 100.0 |
| | | | 0.56 | 97.7 |
| | | | 0.43 | 96.7 |
| | | | 0.28 | 32.7 |
| | | Untreated Control | | 0 |
| Control of Large Crabgrass | 7 | Example 1 | 0.84 + 0.84 + 0.56 | 99.3 |
| | | + Ethalfluralin | 0.56 + 0.84 + 0.56 | 100.0 |
| | | + Linuron | 0.43 + 0.84 + 0.56 | 92.7 |
| | | | 0.28 + 0.84 + 0.56 | 95.3 |
| | | Example 1 | 0.84 | 80.0 |
| | | | 0.56 | 46.7 |
| | | | 0.43 | 43.3 |
| | | | 0.28 | 0 |
| | | Untreated Control | | 0 |
| | 26 | Example 1 | 0.84 + 0.84 + 0.56 | 98.0 |
| | | + Ethalfluralin | 0.56 + 0.84 + 0.56 | 97.3 |
| | | + Linuron | 0.43 + 0.84 + 0.56 | 93.7 |
| | | | 0.28 + 0.84 + 0.56 | 93.3 |
| | | Example 1 | 0.84 | 88.7 |
| | | | 0.56 | 43.3 |
| | | | 0.43 | 30.0 |
| | | | 0.28 | 0 |
| Control of Tall Morningglory | 7 | Untreated Control | | 0 |
| | | Example 1 | 0.84 + 0.84 + 0.56 | 100.0 |
| | | + Ethalfluralin | 0.56 + 0.84 + 0.56 | 100.0 |
| | | + Linuron | 0.43 + 0.84 + 0.56 | 100.0 |
| | | Example 1 | 0.84 | 100.0 |
| | | | 0.56 | 100.0 |
| | | | 0.43 | 100.0 |
| | | | 0.28 | 0 |
| | | Untreated Control | | 0 |
| | 26 | Example 1 | 0.84 + 0.84 + 0.56 | 100.0 |
| | | + Ethalfluralin | 0.56 + 0.84 + 0.56 | 100.0 |
| | | + Linuron | 0.43 + 0.84 + 0.56 | 100.0 |
| | | | 0.28 + 0.84 + 0.56 | 99.3 |
| | | Example 1 | 0.84 | 98.0 |
| | | | 0.56 | 97.0 |
| | | | 0.43 | 97.0 |
| | | | 0.28 | 46.0 |
| Control of Common Purslane | 7 | Untreated Control | | 0 |
| | | Example 1 | 0.84 + 0.84 + 0.56 | 100.0 |
| | | + Ethalfluralin | 0.56 + 0.84 + 0.56 | 100.0 |
| | | + Linuron | 0.43 + 0.84 + 0.56 | 99.7 |
| | | | 0.28 + 0.84 + 0.56 | 98.3 |
| | | Example 1 | 0.84 | 98.7 |
| | | | 0.56 | 78.3 |
| | | | 0.43 | 86.7 |
| | | | 0.28 | 13.3 |
| | | Untreated Control | | 0 |
| | 26 | Example 1 | 0.84 + 0.84 + 0.56 | 100.0 |
| | | + Ethalfluralin | 0.56 + 0.84 + 0.56 | 100.0 |
| | | + Linuron | 0.43 + 0.84 + 0.56 | 100.0 |
| | | | 0.28 + 0.84 + 0.56 | 100.0 |
| | | Example 1 | 0.84 | 100.0 |
| | | | 0.56 | 86.7 |
| | | | 0.43 | 80.0 |
| | | | 0.28 | 31.7 |
| Control of Foxtail Millet | 7 | Untreated Control | | 0 |
| | | Example 1 | 0.84 + 0.84 + 0.56 | 99.0 |
| | | + Ethalfluralin | 0.56 + 0.84 + 0.56 | 96.7 |
| | | + Linuron | 0.43 + 0.84 + 0.56 | 81.0 |
| | | | 0.28 + 0.84 + 0.56 | 88.7 |
| | | Example 1 | 0.84 | 83.3 |
| | | | 0.56 | 30.0 |
| | | | 0.43 | 33.3 |
| | | | 0.28 | 0 |
| | | Untreated Control | | 0 |
| | 26 | Example 1 | 0.84 + 0.84 + 0.56 | 99.0 |
| | | + Ethalfluralin | 0.56 + 0.84 + 0.56 | 96.7 |
| | | + Linuron | 0.43 + 0.84 + 0.56 | 94.3 |
| | | | 0.28 + 0.84 + 0.56 | 94.0 |
| | | Example 1 | 0.84 | 87.7 |
| | | | 0.56 | 43.3 |
| | | | 0.43 | 23.3 |
| | | | 0.28 | 0 |
| Control of Prickly Sida | 7 | Untreated Control | | 0 |
| | | Example 1 | 0.84 + 0.84 + 0.56 | 100.0 |
| | | + Ethalfluralin | 0.56 + 0.84 + 0.56 | 100.0 |
| | | + Linuron | 0.43 + 0.84 + 0.56 | 100.0 |

TABLE XIII-continued

| Observation | Days After Treatment | Treatment | Rate kg/ha | Percent |
|---|---|---|---|---|
| | | | 0.28 + 0.84 + 0.56 | 100.0 |
| | | Example 1 | 0.84 | 100.0 |
| | | | 0.56 | 100.0 |
| | | | 0.43 | 100.0 |
| | | | 0.28 | 0 |
| | | Untreated Control | | 0 |
| | 26 | Example 1 | 0.84 + 0.84 + 0.56 | 100.0 |
| | | + Ethalfluralin | 0.56 + 0.84 + 0.56 | 100.0 |
| | | + Linuron | 0.43 + 0.84 + 0.56 | 100.0 |
| | | | 0.28 + 0.84 + 0.56 | 100.0 |
| | | Example 1 | 0.84 | 100.0 |
| | | | 0.56 | 98.7 |
| | | | 0.43 | 97.3 |
| | | | 0.28 | 49.3 |
| | | Untreated Control | | 0 |

The present compounds and intermediates have also been found to display useful activity as aquatic algicides. It is therefore provided as another embodiment of the invention a method for controlling the growth of aquatic algae which comprises applying to the water containing said algae an algicidal amount of a present compound or intermediate. These active agents are generally applied at rates effective to inhibit the growth of algae without causing significant toxicity to other aquatic life. The compounds and intermediates are applied at rates in the range of from about 20.0 ppm to about 0.1 ppm, more preferably at 10 ppm to 0.5 ppm.

EXPERIMENT 12

The initial screening procedure used to detect aquatic algicidal activity was performed at a test compound concentration of 10 ppm against the algae Chlorella vulgaris (A), Scenedesmus quadricanda (B), Anacystis nidulans (C) and Anabaena flos-aquae (D). Additional species of algae were also tested against at lower concentration rates. These species are as follows:

E. Stichococcus bascillaris
F. Chlamydomonas moewusii
G. Anabaena spp.
H. Anabaena spiroides These species of algae were grown on agar slants containing artificial Hughes' media. Each species of algae was suspended in 5 ml of an aqueous, sterile Hughes' media by washing the agar slants. This solution was then pipetted into a volume of 400 ml of the sterile media. Two ml of the inoculated media was transferred via syringe to a sterilized 12 ml vial, to which 10 μl of the formulated compound was added to obtain a test concentration of 10 ppm. The compounds were formulated by adding 10 mg compound to 0.5 ml acetone and 4.5 ml sterile 0.1 percent Tween 80. Lower concentrations were obtained by further serial dilution. After addition the vial was stoppered.

Observations were made 7 days after treatment and the activity of the test compounds against algae growth is recorded in Table XIV according to the following scale:

1 = no effect
2 = slight effect
3 = moderate effect
4 = heavy control
5 = 100% control

TABLE XIV

| Example No. of Compound Tested | Aquatic Algicide Concentration ppm | Aquatic Algae | | | | | | | |
|---|---|---|---|---|---|---|---|---|---|
| | | A | B | C | D | E | F | G | H |
| 1 | 10.0 | 5 | 5 | 5 | 4 | | | | |
| | 10.0 | 5 | 5 | 5 | | | | | |
| | 1.0 | 4 | 4 | 1 | | | | | |
| | 1.0 | 3 | 4 | 1 | | | 1 | | |
| | 1.0 | | | | 1 | 3 | 1 | 1 | |
| | 0.5 | 4 | 4 | 1 | | | | | |
| | 0.5 | 2 | 1 | 1 | 1 | | | | |
| | 0.5 | | | | 1 | 2 | 1 | 1 | |
| 2 | 10.0 | 5 | 5 | 1 | | | | | |
| 4 | 10.0 | 5 | 5 | 2 | 1 | | | | |
| 6 | 10.0 | 2 | 1 | 1 | 1 | | | | |
| 10 | 10.0 | 1 | 1 | 1 | | | | | |
| 14 | 10.0 | 1 | 1 | 1 | 1 | | | | |
| 17 | 10.0 | 5 | 5 | 5 | 3 | | | | |
| | 1.0 | 1 | 1 | 1 | 1 | | | | |
| | 1.0 | | | | | 3 | 1 | 1 | 1 |
| | 0.5 | 1 | 1 | 1 | 1 | | | | |
| | 0.5 | | | | | 1 | 1 | 1 | 1 |
| 22 | 10.0 | 1 | 1 | 1 | 1 | | | | |
| 23 | 10.0 | 4 | 5 | 4 | 3 | | | | |
| | 1.0 | 1 | 1 | 1 | 1 | | | | |
| | 1.0 | | | | | 1 | 1 | 1 | 1 |
| | 0.5 | 1 | 1 | 1 | 1 | | | | |
| | 0.5 | | | | | 1 | 1 | 1 | 1 |
| 28 | 10.0 | 4 | 4 | 5 | 4 | | | | |
| | 1.0 | 2 | 4 | 1 | 1 | | | | |
| | 1.0 | | | | | 1 | 1 | 1 | 1 |
| | 0.5 | 1 | 4 | 1 | 1 | | | | |
| | 0.5 | | | | | 1 | 1 | 1 | 1 |
| 30 | 10.0 | 1 | 1 | 2 | 1 | | | | |
| 32 | 10.0 | 4 | 4 | 5 | 4 | | | | |
| | 1.0 | | 1 | 1 | 5 | | | | |
| | 1.0 | | | | | 1 | 1 | 1 | 1 |
| | 0.5 | | 1 | 1 | 1 | | | | |
| | 0.5 | | | | | 1 | 1 | 1 | 1 |

The present compounds and intermediates have also exhibited useful aquatic herbicidal activity against a wide variety of undesired aquatic plants. It is therefore provided as another aspect of this invention a method for controlling the growth of aquatic plants which comprises applying to the water containing said plants a growth inhibiting amount of a present compound or intermediate. The term "growth inhibiting amount", as defined herein, refers to an amount of a compound or intermediate of the present invention which either kills or stunts the growth of the aquatic plant for which control is desired. This amount will generally be from about 20.0 ppm to about 0.5 ppm, more preferably at about 10.0 ppm to 1 ppm. It is, of course, apparent that higher or lower concentrations of the active agent can be employed depending on the plant species to be inhibited, the temperature, and the shape and type of the body of water to be treated. At higher water temperatures, for example, less compound is generally required for a given degree of control than is needed at lower temperatures.

In considering the treatment of moving streams for the purpose of controlling flora fixed therein, special account must be taken of the fact that the compounds will pass over the area to be treated and that the concentration during the contact period is dependent upon the water flow rate, the rate of chemical addition, and the time period of addition.

EXPERIMENT 13

Test compounds were evaluated in this screen to detect aquatic herbicidal activity. The compounds were formulated by dissolving them in acetone and aqueous 0.1% Tween 80. This formulation was added to water containing the plant species to be tested against to provide the appropriate test compound concentration.

The following list of aquatic plant species were tested against in this screen:

Hydrilla (*Hydrilla verticillata*)
Coontail (*Ceratophyllum demersum*)
Duckweed (*Lemna minor*)
Southern Naiad (*Najas guadalupensis*)
Eurasian Milfoil (*Myriophyllum specatum*)
Cabomba (*Cabomba caroliniana*)

Observations were made 1, 2 or 3 weeks after treatment. The injury rating was recorded according to the scale above and the results of this experiment appear below in Table XV.

TABLE XV

Aquatic Herbicide

| Example No. of Compound Tested | Concentration ppm | Weeks After Treatment | Hydrilla | Coontail | Duckweed | Southern Naiad | Eurasian Milfoil | Cabomba |
|---|---|---|---|---|---|---|---|---|
| 1 | 10.0 | 1 | 1 | 1 | 1 | | | |
|   | 4.0 | 1 | 1 | 1 | 4 | | | |
|   | 2.0 | 1 | 4 | 1 | 3 | | | |
|   | 2.0 | 1 | 2 | 4 | 1 | 1 | 2 | 3 |
|   |     | 2 | 2 | 3 | 2 | 1 | 3 | 2 |
|   |     | 3 | 3 | 3 | 3 | 2 | 3 | 5 |
|   | 1.0 | 1 | 4 | 4 | 1 | 2 | 4 | 2 |
|   |     | 2 | 3 | 5 | 4 | 2 | 3 | 3 |
|   |     | 3 | 4 | 5 | 4 | 2 | 3 | 3 |
|   | 0.5 | 1 | 3 | 4 | 1 | 1 | 1 | 1 |
|   |     | 2 | 2 | 4 | 1 | 1 | 2 | 1 |
|   |     | 3 | 3 | 3 | 1 | 2 | 3 | 2 |
| 2 | 10.0 | 1 | 1 | 1 | 1 | | | |
| 17 | 4.0 | 1 | 5 | 4 | 4 | | | |
|    | 2.0 | 1 | 3 | 1 | 4 | | | |
| 23 | 4.0 | 1 | 1 | 1 | 1 | | | |
|    | 2.0 | 1 | 1 | 1 | 1 | | | |
| 28 | 4.0 | 1 | 1 | 2 | 2 | | | |
|    | 2.0 | 1 | 1 | 1 | 2 | | | |
| 32 | 4.0 | 1 | 3 | 1 | 1 | | | |
|    | 2.0 | 1 | 2 | 2 | 2 | | | |

I claim:

1. A method for controlling undesired plants which comprises applying to the plants a growth inhibiting amount of 4-chloro-N-[5-(1,1-dimethylethyl)-3-isoxazolyl]-2-methylbutanamide.

2. A method of controlling undesired plants which comprises applying to the plants a growth inhibiting amount of 4-chloro-N-[3-(1,1-dimethylethyl)-5-isoxazolyl]-2-methylbutanamide.

3. A method of controlling undesired plants which comprises applying to the plants a growth inhibiting amount of 4-chloro-N-[3-(1,1-dimethylethyl)-5-isothiazolyl]-2-methylbutanamide.

* * * * *